(12) United States Patent
Cotter et al.

(10) Patent No.: US 12,138,489 B2
(45) Date of Patent: *Nov. 12, 2024

(54) FLUE FOR ULTRASONIC ASPIRATION SURGICAL HORN

(71) Applicant: Integra LifeSciences Enterprises, LLLP, Princeton, NJ (US)

(72) Inventors: Daniel J. Cotter, North Easton, MA (US); Saurav V. Gupta, Medway, MA (US); Igor V. Kosenko, Boxborough, MA (US); John Bertorelli, Andover, MA (US); Prakash Manandhar, Lawrence, MA (US)

(73) Assignee: Integra LifeSciences Enterprises, LLLP, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,594

(22) Filed: Jul. 17, 2023

(65) Prior Publication Data

US 2024/0082606 A1    Mar. 14, 2024

Related U.S. Application Data

(63) Continuation of application No. 17/526,193, filed on Nov. 15, 2021, now Pat. No. 11,738,215, which is a
(Continued)

(51) Int. Cl.
| | |
|---|---|
| *A61N 7/02* | (2006.01) |
| *A61B 17/22* | (2006.01) |
| *A61B 17/32* | (2006.01) |

(52) U.S. Cl.
CPC ........ *A61N 7/022* (2013.01); *A61B 17/22012* (2013.01); *A61B 17/320068* (2013.01);
(Continued)

(58) Field of Classification Search
CPC ...... A61B 17/22012; A61B 17/320068; A61B 2017/22079; A61B 2017/320069;
(Continued)

(56) References Cited

U.S. PATENT DOCUMENTS

| | | |
|---|---|---|
| 4,063,557 A | 12/1977 | Wuchinich et al. |
| 4,223,676 A | 9/1980 | Wuchinich et al. |

(Continued)

FOREIGN PATENT DOCUMENTS

| | | |
|---|---|---|
| EP | 1607075 | 12/2005 |
| EP | 3448283 B1 | 2/2020 |

(Continued)

OTHER PUBLICATIONS

Partial Search for International Application No. PCT/IB2017/057145 dated Jan. 31, 2018.
(Continued)

*Primary Examiner* — Michael J Tsai
*Assistant Examiner* — Rachel T. Smith
(74) *Attorney, Agent, or Firm* — Dinsmore & Shohl LLP

(57) ABSTRACT

A flue for use with an ultrasonic surgical tip, comprising protrusions or bumps on its inner surface with improved protrusion pattern, density and location. The flue has enhanced cooling effect for the ultrasonic surgical tip.

20 Claims, 24 Drawing Sheets

Related U.S. Application Data continuation of application No. 15/496,680, filed on Apr. 25, 2017, now Pat. No. 11,173,327.

(60) Provisional application No. 62/420,691, filed on Nov. 11, 2016, provisional application No. 62/326,988, filed on Apr. 25, 2016.

(52) U.S. Cl.
CPC .............. *A61B 2017/22079* (2013.01); *A61B 2017/320069* (2017.08); *A61B 2017/32007* (2017.08); *A61B 2017/32008* (2013.01); *A61B 2017/320084* (2013.01); *A61B 2217/007* (2013.01); *A61B 2218/002* (2013.01); *A61B 2218/007* (2013.01)

(58) Field of Classification Search
CPC ........... A61B 2017/32007; A61B 2017/32008; A61B 2017/320084; A61B 2217/007; A61B 2218/002; A61B 2218/007; A61N 7/022; A61M 1/0039; A61M 1/0043; A61M 1/0064

See application file for complete search history.

(56) References Cited

U.S. PATENT DOCUMENTS

| | | | |
|---|---|---|---|
| 4,425,115 A | 1/1984 | Wuchinich | |
| 4,516,398 A | 5/1985 | Wuchinich | |
| 4,634,419 A | 1/1987 | Kreizman et al. | |
| 4,734,964 A | 4/1988 | Lane et al. | |
| 4,747,820 A | 5/1988 | Hornlein et al. | |
| 4,750,902 A | 6/1988 | Wuchinich et al. | |
| 4,768,496 A | 9/1988 | Kreizman et al. | |
| 4,827,911 A | 5/1989 | Broadwin et al. | |
| 4,846,790 A | 7/1989 | Hornlein et al. | |
| 4,881,761 A | 11/1989 | Hornlein et al. | |
| 4,921,476 A | 5/1990 | Wuchinich | |
| 4,931,047 A | 6/1990 | Broadwin et al. | |
| 4,978,333 A | 12/1990 | Broadwin et al. | |
| 4,988,334 A * | 1/1991 | Hornlein | A61M 1/86 601/2 |
| 5,015,227 A | 5/1991 | Broadwin et al. | |
| 5,123,903 A | 6/1992 | Quaid et al. | |
| 5,188,589 A | 2/1993 | Wypych et al. | |
| 5,190,517 A | 3/1993 | Zieve et al. | |
| 5,221,282 A | 6/1993 | Wuchinich | |
| 5,421,829 A | 6/1995 | Olichney et al. | |
| 5,466,020 A | 11/1995 | Page et al. | |
| 5,484,398 A | 1/1996 | Stoddard | |
| D367,323 S | 2/1996 | Carr et al. | |
| 5,492,528 A | 2/1996 | Anis | |
| 5,984,904 A * | 11/1999 | Steen | A61F 9/00745 604/523 |
| 6,083,191 A | 7/2000 | Rose | |
| 6,177,755 B1 | 1/2001 | Hur | |
| D438,952 S | 3/2001 | Cimino et al. | |
| 6,214,017 B1 | 4/2001 | Stoddard et al. | |
| 6,256,859 B1 | 7/2001 | Stoddard et al. | |
| 6,319,223 B1 | 11/2001 | Wortrich et al. | |
| 6,468,059 B2 | 10/2002 | Haser et al. | |
| 6,499,358 B1 | 12/2002 | Hogan et al. | |
| D477,867 S | 7/2003 | O'Mahony et al. | |
| 6,595,957 B1 | 7/2003 | Griffiths et al. | |
| 6,602,227 B1 | 8/2003 | Cimino et al. | |
| D479,320 S | 9/2003 | O'Mahony et al. | |
| 6,654,999 B2 | 12/2003 | Stoddard et al. | |
| 6,723,110 B2 | 4/2004 | Timm et al. | |
| 7,204,825 B2 | 4/2007 | Cimino et al. | |
| D557,803 S | 12/2007 | Muri et al. | |
| D557,804 S | 12/2007 | Muri et al. | |
| 7,442,168 B2 | 10/2008 | Novak et al. | |
| 7,871,392 B2 | 1/2011 | Sartor | |
| 8,092,475 B2 | 1/2012 | Cotter et al. | |
| 8,118,823 B2 | 2/2012 | Cotter et al. | |
| 8,142,460 B2 | 3/2012 | Cotter et al. | |
| 8,211,103 B2 | 7/2012 | Greep | |
| D675,728 S | 2/2013 | Tout et al. | |
| 8,518,066 B2 | 8/2013 | Cotter et al. | |
| D699,836 S | 2/2014 | Burger et al. | |
| 9,149,291 B2 | 10/2015 | Parham et al. | |
| 9,421,027 B2 | 8/2016 | Cotter et al. | |
| 11,173,327 B2 | 11/2021 | Cotter et al. | |
| 11,738,215 B2 * | 8/2023 | Cotter | A61N 7/022 604/22 |
| 2002/0002369 A1 | 1/2002 | Hood | |
| 2006/0052774 A1 | 3/2006 | Garrison et al. | |
| 2006/0063973 A1 | 3/2006 | Makower et al. | |
| 2008/0200884 A1 | 8/2008 | Perkins et al. | |
| 2011/0160620 A1 | 6/2011 | Gill et al. | |
| 2014/0277034 A1 | 9/2014 | Darian | |
| 2015/0080925 A1 | 3/2015 | Schulte et al. | |
| 2015/0328048 A1 | 11/2015 | Koplin | |
| 2016/0059043 A1 | 3/2016 | Gill | |
| 2017/0304655 A1 | 10/2017 | Cotter et al. | |
| 2017/0333606 A1 | 11/2017 | Manandhar et al. | |
| 2017/0354429 A1 | 12/2017 | Ketelhohn et al. | |

FOREIGN PATENT DOCUMENTS

| | | |
|---|---|---|
| JP | 2-139615 | 11/1990 |
| JP | 7-501460 | 2/1995 |
| WO | 9306799 | 4/1993 |
| WO | 9308750 A2 | 5/1993 |
| WO | 9517855 | 7/1995 |
| WO | 2004045705 | 6/2004 |
| WO | 2010057211 A1 | 5/2010 |
| WO | 2011005467 A2 | 1/2011 |
| WO | 2014134292 | 9/2014 |
| WO | 2015061258 | 4/2015 |
| WO | 2017187345 | 11/2017 |
| WO | 2017203408 | 11/2017 |

OTHER PUBLICATIONS

European Patent Office, International Search Report and Written Opinion for PCT/IB2017/057145 dated Mar. 15, 2018, mailed Mar. 23, 2018, Rijswijk, NL.
Transmittal Letter of Related Cases dated Jan. 30, 2019.
IP Australia, Exmination report No. 1 for patent application No. 2017257421 dated Mar. 11, 2021.
State Intellectual Property Office, Chinese First Office Action for application No. 201780036141.0 dated Sep. 29, 2020.
Japanese Notice of Reasons for Rejection for application No. 2018-555560 mailed Feb. 2, 2021.
International Search Report and Written Opinion for PCT/182017/052382 dated Aug. 17, 2017.
International Search Report and Written Opinion for PCT/182017/052980 dated Jul. 19, 2017.
International Search Report and Written Opinion for PCT/IB2017/053510 dated Nov. 13, 2017.
Partial Search Report for PCT/182017/053510 dated Sep. 22, 2017,.
Franasiak, Jason M.; Ergonomic Strain in Minimally Invasive Surgery: Addressing the Strain Epidemic; www.jcomjournal.com; vol. 22, No. 6, pp. 267-273, Jun. 2015.
Krautkramer J. and Krautkramer H. Ultrasonic Testing of Materials, 1983.
Berguer, R.; Ergonomic problems associated with laparoscopic surgery; Surgical Endoscopy, 1999 13:466-468; 1999.
Integra Lifesciences Corporation; CUSA Excel Ultrasonic Surgical Aspiration System, CUSA EXcel System User's Guide, 6 pages, 2007.
Integra Lifesciences Corporation; CUSA Excel+ Ultrasonic Surgical Aspirator, 8 pages, 2012.
SonaStar; Ultrasonic surgical aspiration system; Accuracy Matters, 2015.

* cited by examiner

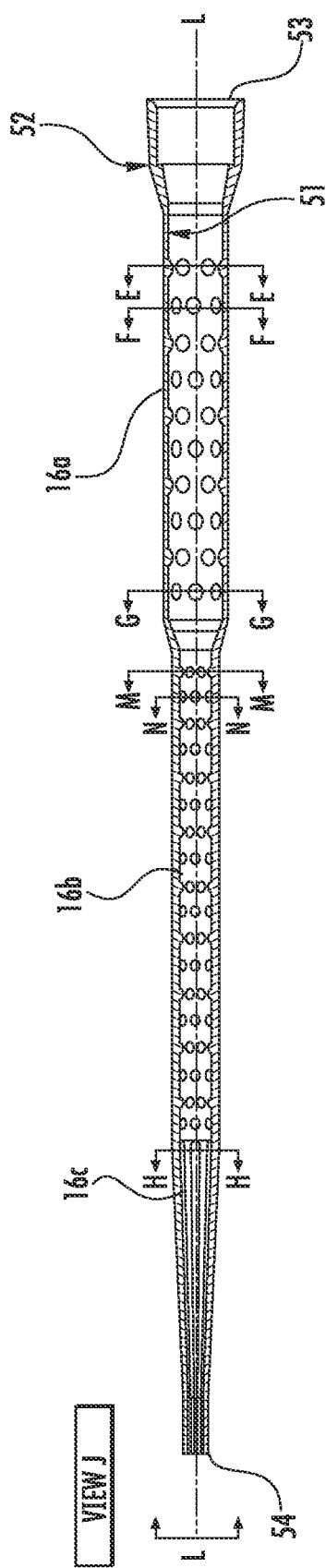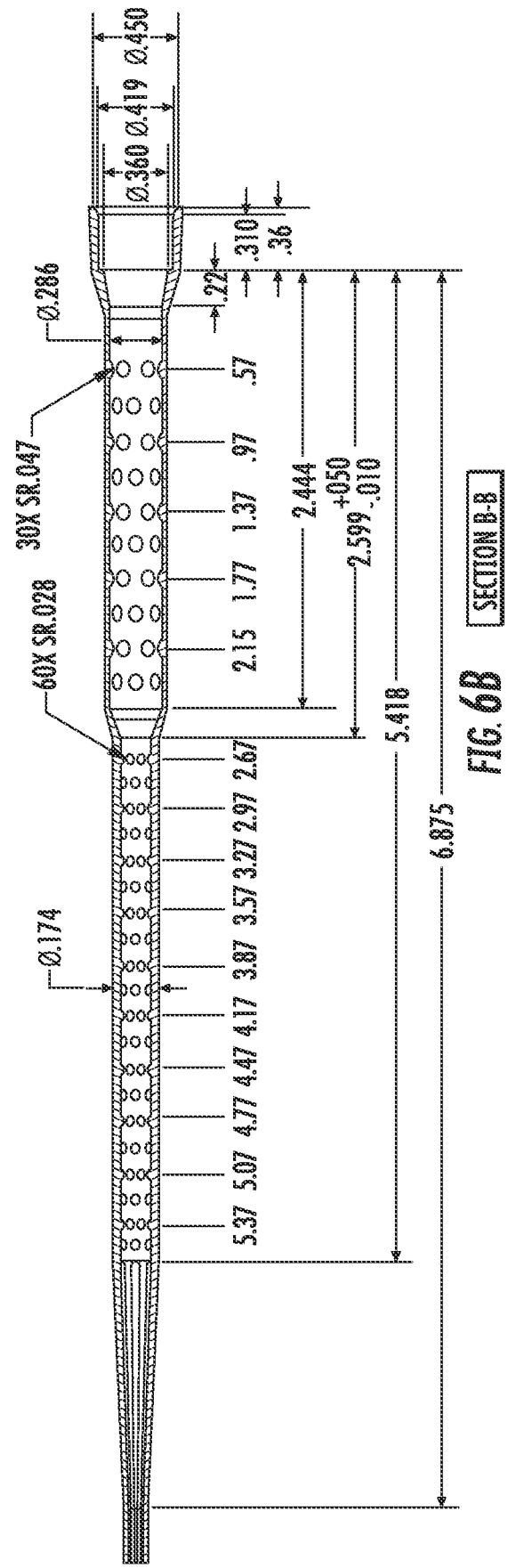
FIG. 6A
FIG. 6B

DETAIL Q

SECTION G-G

SECTION F-F

SECTION E-E

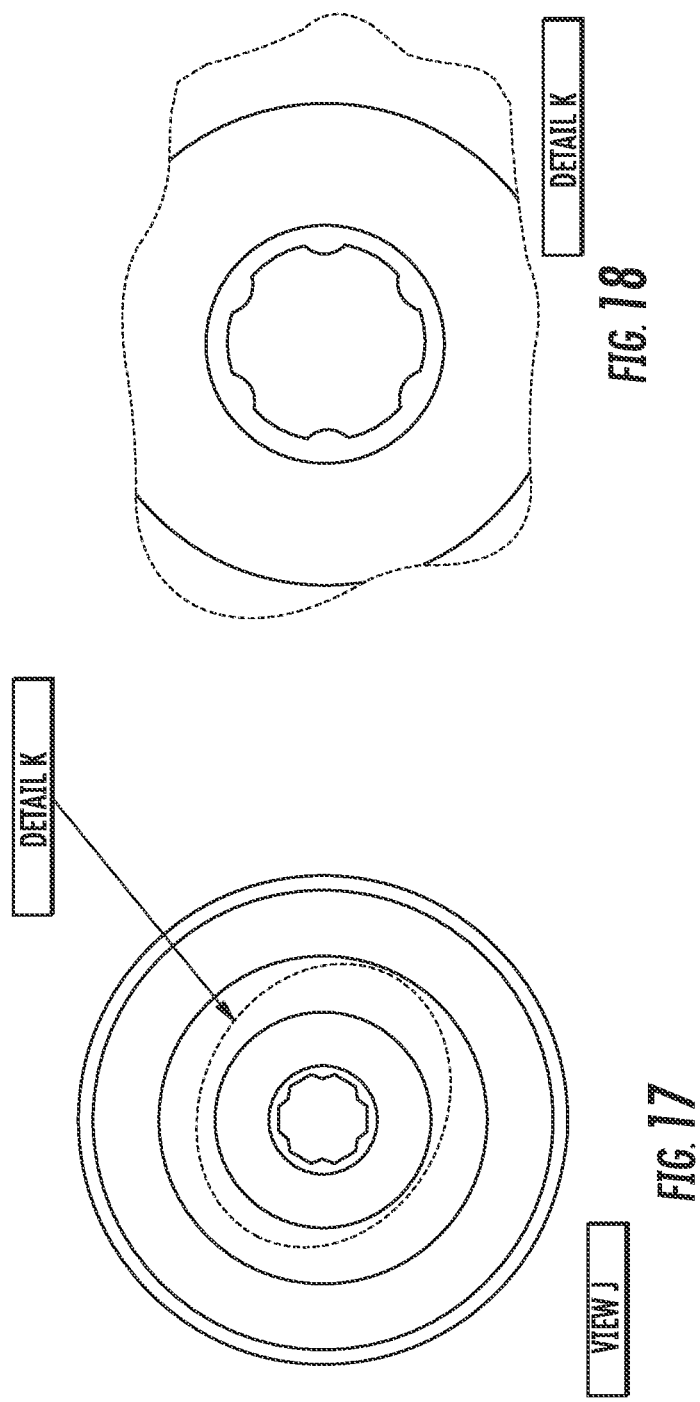

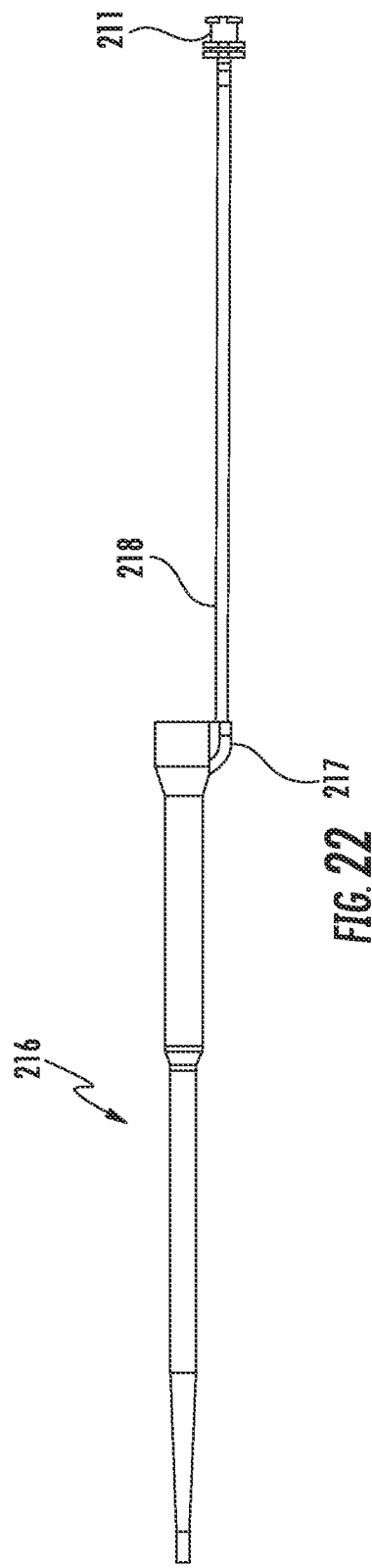

FLUE FOR ULTRASONIC ASPIRATION SURGICAL HORN

CROSS-REFERENCE TO RELATED APPLICATIONS

This application is a continuation patent application of and claims priority and benefit under 35 U.S.C. § 120 to copending U.S. patent application Ser. No. 17/526,193 filed on Nov. 15, 2021, which claims priority to U.S. patent application Ser. No. 15/496,680 (now U.S. Pat. No. 11,173,327) filed on Apr. 25, 2017, which claims priority to and benefit under 35 U.S.C. § 119(e) to U.S. Provisional Application No. 62/326,988, filed Apr. 25, 2016, and U.S. Provisional Application No. 62/420,691, filed Nov. 11, 2016, the entire contents of which are hereby incorporated by reference.

BACKGROUND OF THE INVENTION

The present invention relates generally to ultrasonic surgical devices, and more particularly, to ultrasonic surgical aspirators for removing diseased tissues.

Devices that effectively utilize ultrasonic energy for a variety of applications are well known in a number of diverse arts. One of these devices is an ultrasonic horn or tip used for the removal of tissue. The Ampulla or Gaussian profile was published by Kleesattel as early as 1962, and is employed as a basis for many ultrasonic horns in surgical applications including devices for use in ultrasonic aspiration as described in U.S. Pat. No. 4,063,557 to Wuchinich, et al, 1977, and U.S. Pat. No. 6,214,017 to Stoddard, et al, 2001, which are incorporated herein by reference. The Gaussian profile is used in practice to establish and control the resonance and mechanical gain of horns. A resonator, a connecting body, and the horn act together as a three-body system to provide a mechanical gain, which is defined as the ratio of output stroke amplitude of the distal end of the tip to the input amplitude of the resonator. The mechanical gain is the result of the strain induced in the materials of which the resonator, the connecting body, and the ultrasonic horn are composed.

A magnetostrictive transducer coupled with the connecting body functions as a first stage of the booster horn with a mechanical gain of about 2:1, due to the reduction in area ratio of the wall of the complex geometry. The major diameter of the horn transitions to the large diameter of the Gaussian segment in a stepped-horn geometry with a gain of as large as about 5:1, again due to reduction in area ratio. The uniform strain along the length of the Gaussian provides multiplicative gain of typically less than 2:1. Thus, the application of ultrasonically vibrating surgical devices used to fragment and remove unwanted tissue with significant precision and safety has led to the development of a number of valuable surgical procedures.

Certain devices known in the art characteristically produce continuous vibrations having substantially constant amplitude at a frequency of about twenty to about fifty-five kHz, for example, at a predetermined frequency of 20-36 kHz. Amplitude of transducer-surgical tip systems decrease with increasing frequency because maximum stress in the material of the horns is proportional to amplitude times frequency, and the material must be maintained to an allowed fraction of its yield strength to support rated life in view of material fatigue limits. For example, U.S. Pat. Nos. 4,063,557, 4,223,676 and 4,425,115, which are incorporated herein by reference, disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

Ultrasonic aspiration has become the standard of care for removal of tumors and diseased tissue in neurosurgery and general surgery. Typically, ultrasonic surgical aspirators for fragmenting and aspirating tissue include an ultrasonic transducer supported within a handpiece, an ultrasonically vibrating horn or tip operably connected to the ultrasonic transducer, and a sleeve or flue positioned about the horn. The horn includes a longitudinally extending central bore having one end located adjacent a distal tip and a second end located adjacent the proximal end of the horn. The proximal end of the horn is adapted to engage a vacuum source to facilitate aspiration of fluid. The flue is positioned about the horn to define an annular passage. Irrigation fluid is supplied through the annular passage around the horn to the surgical site where it mixes with blood and tissue particles and is aspirated through the bore in the horn. By mixing the irrigation fluid with the blood and tissue particles, coagulation of the blood is slowed down and aspiration thereof is aided. U.S. Pat. Nos. 5,015,227 and 4,988,334 disclose such ultrasonic surgical devices and are incorporated herein by reference. For example, a titanium surgical tip may be powered by a transducer to fragment tissue and suction effluent via a central channel. A flue is employed to deliver irrigation liquid, usually saline, and it protects tissue along the path to the surgical site from the vibrating surgical tip. The transducer vibrates along its length, and ultrasonic horns such as stepped horns and specialty profiles of reduced diameter amplify vibration.

A known instrument on the market for the ultrasonic fragmentation of tissue at an operation site and aspiration of the tissue particles and fluid away from the site is the CUSA® Excel Ultrasonic Surgical Aspirator (Integra Life-Sciences Corporation, Plainsboro, N.J.). When the longitudinally vibrating tip in such an aspirator is brought into contact with tissue, it gently, selectively, and precisely fragments and removes the tissue. The CUSA transducer amplitude can be adjusted independently of the frequency and this amplitude can be maintained under load depending on reserve power of the transducer. In simple harmonic motion devices, the frequency is independent of amplitude. Advantages of this unique surgical instrument include minimal damage to healthy tissue in a tumor removal procedure, skeletoning of blood vessels, prompt healing of tissue, minimal heating or tearing of margins of surrounding tissue, minimal pulling of healthy tissue, and excellent tactile feedback for selectively controlled tissue fragmentation and removal.

In an apparatus that fragments tissue by the ultrasonic vibration of a tool tip, efficiency of energy utilization is optimized when the transducer which provides the ultrasonic vibration operates at resonant frequency. The transducer and surgical tip design establishes the resonant frequency of the system, while the generator tracks the resonant frequency and produces the electrical driving signal to vibrate the transducer at the resonant frequency. However, changes in operational parameters, such as changes in temperature, thermal expansion, and load impedance, result in deviations in the resonant frequency. Accordingly, controlled changes in the frequency of the driving signal are required to track the resonant frequency. This is controlled automatically in the generator.

Conventional ultrasonic surgical aspirating tips employed in surgery for many years typically present a longitudinally vibrating annular surface with a central channel providing suction or aspiration, which contacts tissue and enables fragmentation via described mechanisms of mechanical impact (momentum), cavitation, and ultrasound propagation. Mechanical impact may be most useful in soft tissue and cavitation clearly contributes to the fragmentation of tenacious and hard tissue in situations where liquids are present and high intensity ultrasound exceeds the cavitation threshold.

Ultrasound propagation is concerned with the transmission of pressure across the boundary of a surgical tip and tissue, which leads to the propagation of pressure and, perhaps more importantly, particle displacement. Acoustic impedance is the total reaction of a medium to acoustic transmission through it, represented by the complex ratio of the pressure to the effective flux, that is, particle velocity times surface area through the medium. As discussed in the classic text of Krautkramer J. and Krautkramer H, ULTRASONIC TESTING OF MATERIALS, Berlin, Heidelberg, N.Y., 1983, for the case of a low to high acoustic impedance boundary, it may seem paradoxical that pressure transmitted can exceed 100%, but that is what results from the build-up of pressure from a low to high acoustic impedance boundary. In the case of a high to low acoustic impedance mismatch, such as with a high impedance titanium ultrasonic horn to low impedance fibrous muscle, soft tissue, or water, the pressure transmitted decreases (e.g., less than 15% for titanium to fibrous muscle) and particle displacement increases (e.g., as great as 186% for titanium to muscle).

Heating may occur along the ultrasonic surgical tips. In addition, sometimes a surgeon will compress the flue to tissue during vibration of the surgical tip causing thermal rise. Such heating or thermal rise could cause burns in tissues in contact with the ultrasonic surgical tips. For example, excessive compression in endonasal approaches where the tip and flue are angulated to work off mid-line could possibly lead to burns of the turbinate or nasal passages.

Hence, those skilled in the art have recognized a need for reducing heating along an ultrasonic aspiration tip. The present invention fulfills this need and others.

SUMMARY OF THE INVENTION

In some embodiments of the invention, for example, a flue for use with an ultrasonic horn may comprise an internal surface, a proximal end, and a distal end. In some embodiments, the flue may comprise a first flue extender and a second flue extender. Moreover, in some embodiments, the second flue extender may extend distally from the first flue extender. In various embodiments, the second flue extender may have an internal diameter smaller than an internal diameter of the first flue extender. In addition, in some embodiments, the internal surface of the second flue extender may comprise an arcuate region and a plurality of protrusions forming a bridge.

In addition, in various embodiments, the flue may be in combination with an ultrasonic horn, wherein the ultrasonic horn may include an external surface and may comprise a first horn extender and a second horn extender that may extend distally from the first horn extender. Further in some embodiments, the second horn extender may have an external diameter smaller than an external diameter of the first horn extender. Further, in some embodiments, the first and second flue extenders may be configured to at least partially enclose the first and second horn extenders, respectively. In various embodiments, the bridge may limit contact between the arcuate region of the internal surface of the second flue extender and the external surface of the second horn extender. In some embodiments, the plurality of protrusions may be distributed in staggered rows and columns such that one protrusion is centered about every four adjacent protrusions arranged in a substantially square or rectangular manner. Moreover, in various embodiments, the plurality of protrusions may form the bridge both longitudinally and axially. In some embodiments, the plurality of protrusions may be spherical protrusions. In various embodiments, the internal surface of the first flue extender may comprise an arcuate region and a plurality of protrusions forming a bridge that limits contact with the arcuate region of the internal surface of first flue extender. Moreover, in some embodiments, the plurality of protrusions on the first flue extender may have a spherical radius in the range of about 0.01 inches to about 0.10 inches and the plurality of protrusions on the second flue extender may have a spherical radius in the range of about 0.01 inches to about 0.08 inches. In various embodiments, the internal surface of the first flue extender may comprise an arcuate region and a plurality of protrusions forming a bridge that limits contact with the arcuate region of the internal surface of first flue extender. Further, in some embodiments, the plurality of protrusions on the first flue extender may be larger than the plurality of protrusions on the second flue extender. In various embodiments, at least a part of the internal surface of the second flue extender may have at least three protrusions of the plurality of protrusions per square centimeter. In some embodiments, the internal surface of the first flue extender may comprise an arcuate region and a plurality of protrusions forming a bridge that limits contact with the arcuate region of the internal surface of first flue extender. Further, in various embodiments, the second flue extender may have a higher density of the plurality of protrusions than the first flue extender.

In various embodiments, a flue for use with an ultrasonic horn may comprise an internal surface, wherein the internal surface may include an arcuate region and a plurality of protrusions. In some embodiments, the plurality of protrusions may be distributed at locations that correspond to locations on or about a node of the ultrasonic horn. Further, in some embodiments, the plurality of protrusions may form one or more bridges.

In addition, in some embodiments, the flue may be in combination with an ultrasonic horn having an external surface. In various embodiments, the flue may be configured to be disposed about the external surface of the ultrasonic horn. Further, in some embodiments, the plurality of protrusions form one or more bridges that may limit contact between the arcuate region of the internal surface of the flue and the external surface of the ultrasonic horn. In some embodiments, the plurality of protrusions of the internal surface may be at locations that correspond to locations on or near an antinode of the ultrasonic horn. In various embodiments, the plurality of protrusions of the internal surface may be at locations that correspond to locations of high strain gradient and motion. Further, in some embodiments, the plurality of protrusions of the internal surface may be at locations that correspond to locations on or near the node, on or near an antinode, and between the node and the antinode of the ultrasonic horn. In various embodiments, the plurality of protrusions may be distributed in staggered rows and columns such that one protrusion is centered about every four adjacent protrusions arranged in a substantially square or rectangular manner. Moreover, in some embodiments, the plurality of protrusions may form one or more bridges both longitudinally and axially. In various embodiments, the plurality of protrusions may be spherical protrusions. Further, in some embodiments, the flue may include a first flue extender and a second flue extender extending distally from the first flue extender. In some embodiments, the plurality of protrusions on the first flue extender may have a spherical radius in the range of about 0.01 inches to about 0.10 inches and the plurality of protrusions on the second flue extender may have a spherical radius in the range of about 0.01 inches to about 0.08 inches.

In some embodiments, an ultrasonic surgical apparatus may comprise an ultrasonic horn having an external surface. In various embodiments, the ultrasonic horn may comprise a first horn extender and a second horn extender. Moreover, in some embodiments, the second horn extender may extend distally from the first horn extender. Further, in some embodiments, the second horn extender may have an external diameter smaller than an external diameter of the first horn extender. Moreover, in various embodiments, a flue may have an internal surface, a proximal end, and distal end. In some embodiments, the flue may comprise a first flue extender and a second flue extender. Further, in some embodiments, the second flue extender may extend distally from the first flue extender. In various embodiments, the second flue extender may have an internal diameter smaller than an internal diameter of the first flue extender. In some embodiments, the first and second flue extenders may be configured to at least partially enclose the first and second horn extenders, respectively. Further in some embodiments, the internal surface of the second flue extender may comprise an arcuate region and a plurality of protrusions forming a bridge that limits contact between the arcuate region of the internal surface of the second flue extender and the external surface of the second horn extender.

In addition, in various embodiments, the plurality of protrusions may be distributed in staggered rows and columns such that one protrusion is centered about every four adjacent protrusions arranged in a substantially square or rectangular manner. In some embodiments, the plurality of protrusions may form the bridge both longitudinally and axially. In various embodiments, the plurality of protrusions may be spherical protrusions. In some embodiments, the internal surface of the first flue extender may comprise an arcuate region and a plurality of protrusions forming a bridge that limits contact between the arcuate region of the internal surface of first flue extender and the external surface of the first horn extender. Further, in some embodiments, the plurality of protrusions on the first flue extender may have a spherical radius in the range of about 0.01 inches to about 0.10 inches and the plurality of protrusions on the second flue extender may have a spherical radius in the range of about 0.01 inches to about 0.08 inches. Further, in some embodiments, the plurality of protrusions on the first flue extender may be larger than the plurality of protrusions on the second flue extender. In various embodiments, at least a part of the internal surface of the second flue extender may have at least three protrusions of the plurality of protrusions per square centimeter. Further, in some embodiments, the second flue extender may have a higher density of the plurality of protrusions than the first flue extender.

In various embodiments, an ultrasonic surgical apparatus may comprise an ultrasonic horn having an external surface and a flue having an internal surface. In some embodiments, the flue may be configured to be disposed about the external surface of the ultrasonic horn. Moreover, in various embodiments, the internal surface may include an arcuate region and a plurality of protrusions. In some embodiments, the plurality of protrusions may be distributed at locations that correspond to locations on or near a node of the ultrasonic horn. Further, in various embodiments, the plurality of protrusions may form a bridge that limits contact between the arcuate region of the internal surface of the flue and the external surface of the ultrasonic horn.

In addition, in some embodiments, the internal surface of the flue may further comprise the plurality of protrusions at locations that correspond to locations on or about an antinode of the ultrasonic horn. In some embodiments, the internal surface of the flue may further comprise the plurality of protrusions at locations that correspond to locations of high strain gradient and motion. In various embodiments, the internal surface of the flue may comprise the plurality of protrusions at locations that correspond to locations on or near the node, on or near an antinode, and between the node and the antinode of the ultrasonic horn. Moreover, in some embodiments, the plurality of protrusions may be distributed in staggered rows and columns such that one protrusion is centered about every four adjacent protrusions arranged in a substantially square or rectangular manner. Further, in some embodiments, the plurality of protrusions may form the bridge both longitudinally and axially. In various embodiments, the plurality of protrusions may be spherical protrusions. In some embodiments, the flue may include a first flue extender and a second flue extender extending distally from the first flue extender. Further in some embodiments, the plurality of protrusions on the first flue extender may have a spherical radius in the range of about 0.01 inches to about 0.10 inches and the plurality of protrusions on the second flue extender may have a spherical radius in the range of about 0.01 inches to about 0.08 inches.

In various embodiments, a flue for use with an ultrasonic horn may comprise an internal surface extending between a proximal end and an opposing distal end. In some embodiments, the flue may include a first flue extender and a second flue extender. Moreover, in some embodiments, the second flue extender may extend distally from the first flue extender. Further, in various embodiments, the internal surface of each one of the first flue extender and the second flue extender may include an arcuate region defining a first inner diameter and a plurality of protrusions projecting inwardly from the arcuate region defining a second inner diameter, wherein the second inner diameter is smaller than the first inner diameter.

In addition, in some embodiments, the first inner diameter of the first flue extender may be larger than the first inner diameter of the second flue extender. In various embodiments, the plurality of protrusions may define a plurality of columns and a plurality of rows within each one of the first flue extender and the second flue extender. Moreover, in some embodiments, the plurality of protrusions on the first flue extender may have a spherical radius in the range of about 0.01 inches to about 0.10 inches and the plurality of protrusions on the second flue extender may have a spherical radius in the range of about 0.01 inches to about 0.08 inches. In some embodiments, the second flue extender may have a higher density of the plurality of protrusions than the first flue extender.

Briefly and in general terms, the present invention is directed to flues for use with ultrasonic aspiration surgical horns for cooling the horn. In more detailed aspects, the flues have protrusions or bumps on the internal surface with enhanced protrusion pattern, density and locations that help control thermal rise in the ultrasonic horn. In yet more detailed aspects, the protrusions form a bridge at locations other than simply about the antinode and high motion areas, as they are also in high strain areas. The flues incorporate increased density of protrusions, a more complex load resistant pattern, and extension of the protrusion pattern to the extender regions of high strain. The protrusion pattern is more difficult to spread than the prior art devices.

In accordance with aspects of the present invention, there is provided a flue for use with an ultrasonic horn having an external surface and comprising a first horn extender and a second horn extender extending distally from the first horn extender and having a diameter smaller than the diameter of the first horn extender, the flue having an internal surface, a proximal end and distal end and comprising a first flue extender and a second flue extender extending distally from the first flue extender and having a diameter smaller than the diameter of the first flue extender, the first and second flue extenders being configured to at least partially enclose the first and second horn extenders, wherein the internal surface of the second flue extender comprises a arcuate region and a plurality of protrusions forming a bridge that limits contact between the arcuate region of the internal surface of second flue extender and the external surface of the second horn extender. In preferred embodiments, the protrusions on the first flue extender are larger than the protrusions on the second extender, and the second flue extender has a higher density of protrusions than the first flue extender.

In accordance with other aspects of the present invention, there is provided a flue for use with an ultrasonic horn, the horn having an external surface, the flue having an internal surface, being configured to be disposed about the external surface of the ultrasonic horn, and comprising an arcuate region and protrusions on its internal surface, wherein the protrusions are distributed at locations that correspond to locations on or near a node of the ultrasonic horn, and wherein the protrusions form a bridge that limits contact between the arcuate region of the internal surface of the flue and the external surface of the ultrasonic horn. The flue may further comprise protrusions on its internal surface at locations that correspond to locations on or near an antinode of the ultrasonic horn, and/or at locations that correspond to locations of high strain gradient and motion, such as between nodes and antinodes of the ultrasonic horn.

In more detailed aspects, the protrusions on the internal surface of the flue are distributed in staggered rows and columns such that one protrusion is centered about every four adjacent protrusions arranged in a substantially square or rectangular manner. The plurality of protrusions may form bridges both longitudinally and axially.

In accordance with other aspects of the present invention, there is provided ultrasonic surgical apparatus which comprises a flue as described above and the corresponding ultrasonic horn about which the flue is disposed.

Other features and advantages of the present invention will become more apparent from the following detailed description of the invention, when taken in conjunction with the accompanying exemplary drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

Embodiments of the presently disclosed shear stress ultrasonic horn are described herein with reference to the drawings, in which:

FIG. 6A shows a cross-sectional view taken at section line B-B of FIG. 5A;

FIG. 6B indicates certain measurements (in inches) of the flue of FIG. 6A;

FIG. 17 is a view of the flue of FIG. 6A from the distal end;

FIG. 18 is a detailed illustration of a section of the view of FIG. 17;

FIG. 22 illustrates the flue of FIG. 20 with a flue tube connect to it;

DETAILED DESCRIPTION OF THE PREFERRED EMBODIMENTS

Figure 1:
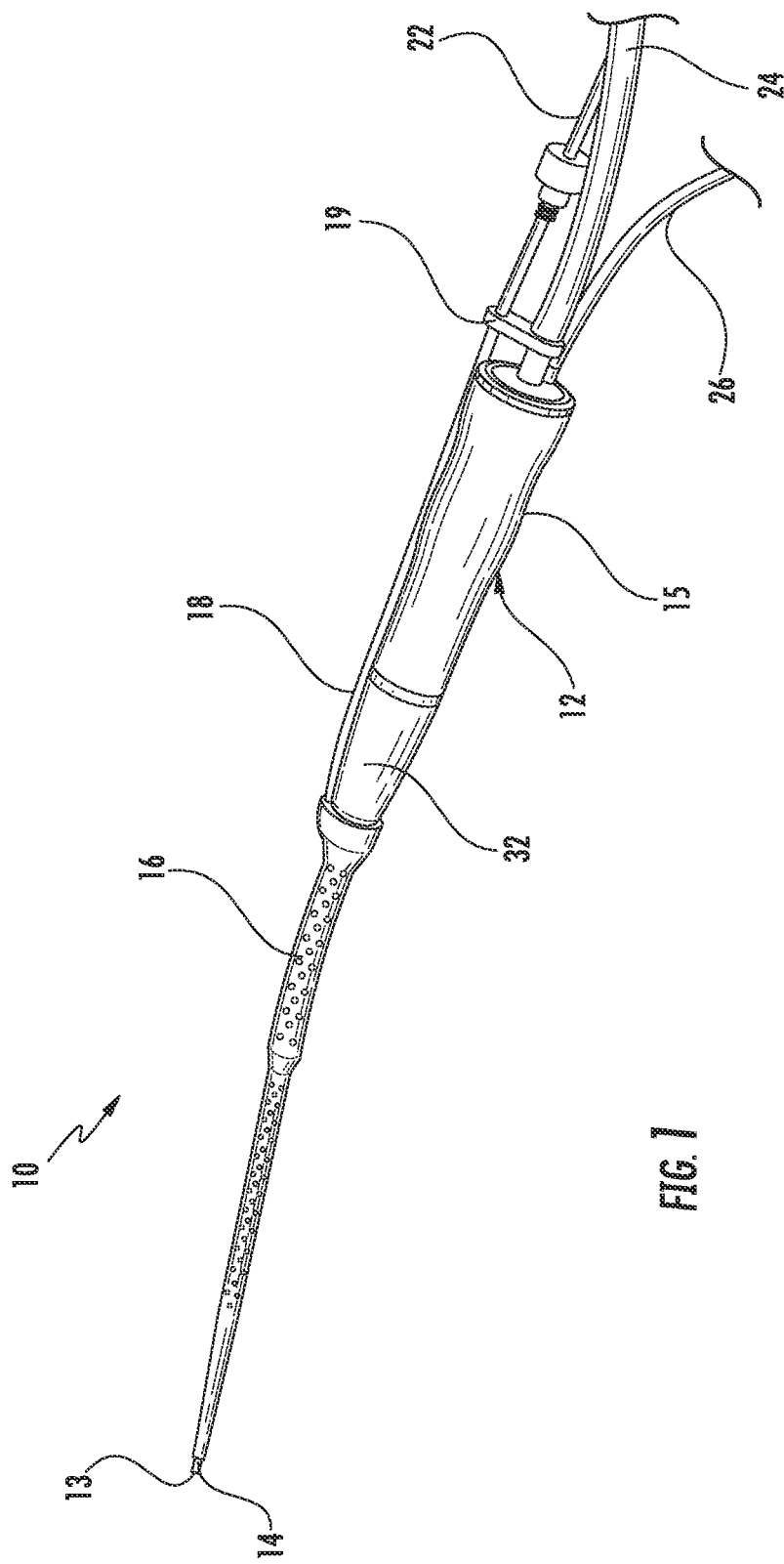
FIG. 1 is a perspective view of an ultrasonic apparatus in accordance with the present invention.

Embodiments of the presently disclosed ultrasonic horn will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic tip," "ultrasonic aspirating tip," "ultrasonic surgical aspirating tip," "aspirating tip," "ultrasonic surgical tip," "surgical tip" and "tip" are used herein interchangeably. The terms "flue," "irrigation flue," "sleeve," "irrigation manifold" and "manifold" are used herein interchangeably. The terms "tip extender" and "horn extender" are used herein interchangeably.

Figure 2:
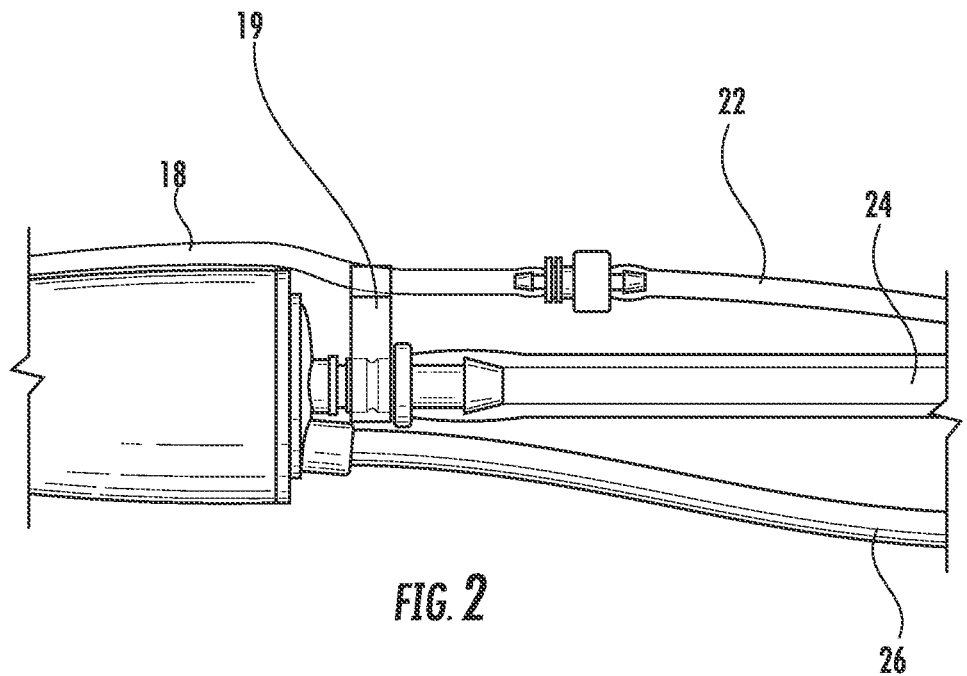
FIG. 2 illustrates the proximal end of the apparatus of FIG. 1 in more detail.
Figure 3:
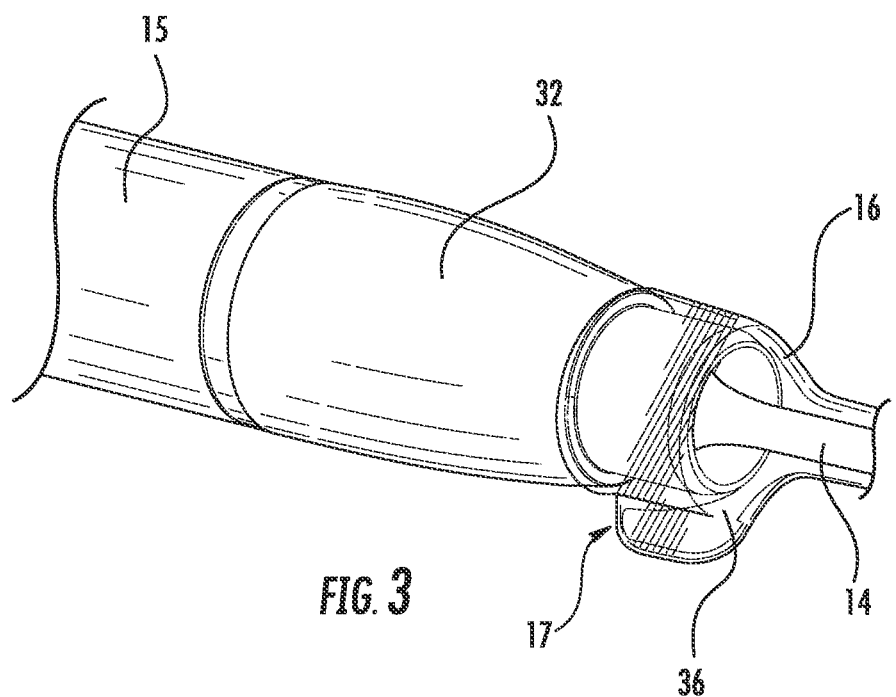
FIG. 3 is a perspective view a nosecone fully assembled to a handpiece and supporting the flue (the flue tube is not shown in this drawing)

Referring now to FIGS. 1-3, one embodiment of the presently disclosed apparatus for ultrasonically fragmenting and aspirating tissue is shown. The present disclosure is directed to an ultrasonic surgical apparatus 10 for ultrasonically fragmenting and aspirating tissue in a surgical operation. Generally the ultrasonic surgical apparatus includes a handpiece 12 used by a surgeon to direct fragmentation. The handpiece 12 encases a transducer (not shown) on which a surgical tip or ultrasonic horn 14 is fastened. The ultrasonic horn can be powered by the transducer and be ultrasonically actuated to fragment tissue and suction effluent via a central channel. A distal end portion 13 of the ultrasonic horn 14 extends beyond a distal end of the flue 16. The ultrasonic horn 14 is vibrated to fragment tissue during surgery. The ultrasonic horn may be made of titanium or other conventional materials known in the art.

A cooling and irrigation system which provides cooling fluid to the ultrasonic horn 14 is provided for maintaining temperature within an acceptable range. The handpiece 12 includes a housing 15 which may be formed of a sterilizable plastic or metal, but is preferably plastic. The flue 16 provides a path for irrigation fluid or liquid and connects to the distal end of the housing 15. The flue 16 typically interfaces to the handpiece 12 via a nosecone 32. The flue 16 may include or attach to a flue tube 18 and be in fluid communication with the flue tube 18 through an opening 17. The nosecone 32 attaches to the handpiece 12 and covers the internal portion of the ultrasonic horn 14.

An irrigation tube 22 connects to the flue tube 18 upstream and supplies irrigation fluid through the flue tube 18 to an operative site during surgery. An aspiration tube 24 provides suction and a path for aspiration from the operative site to a collection canister (not shown). Alternatively, the aspiration tube may be mounted externally of the housing 15. A flue tube clip 19 allows for adjustment of the location of the flue tube 18 per the desires of the surgeon during operation. Also shown is an electrical cable 26 for providing power to the apparatus or providing switching connections.

Figure 4:
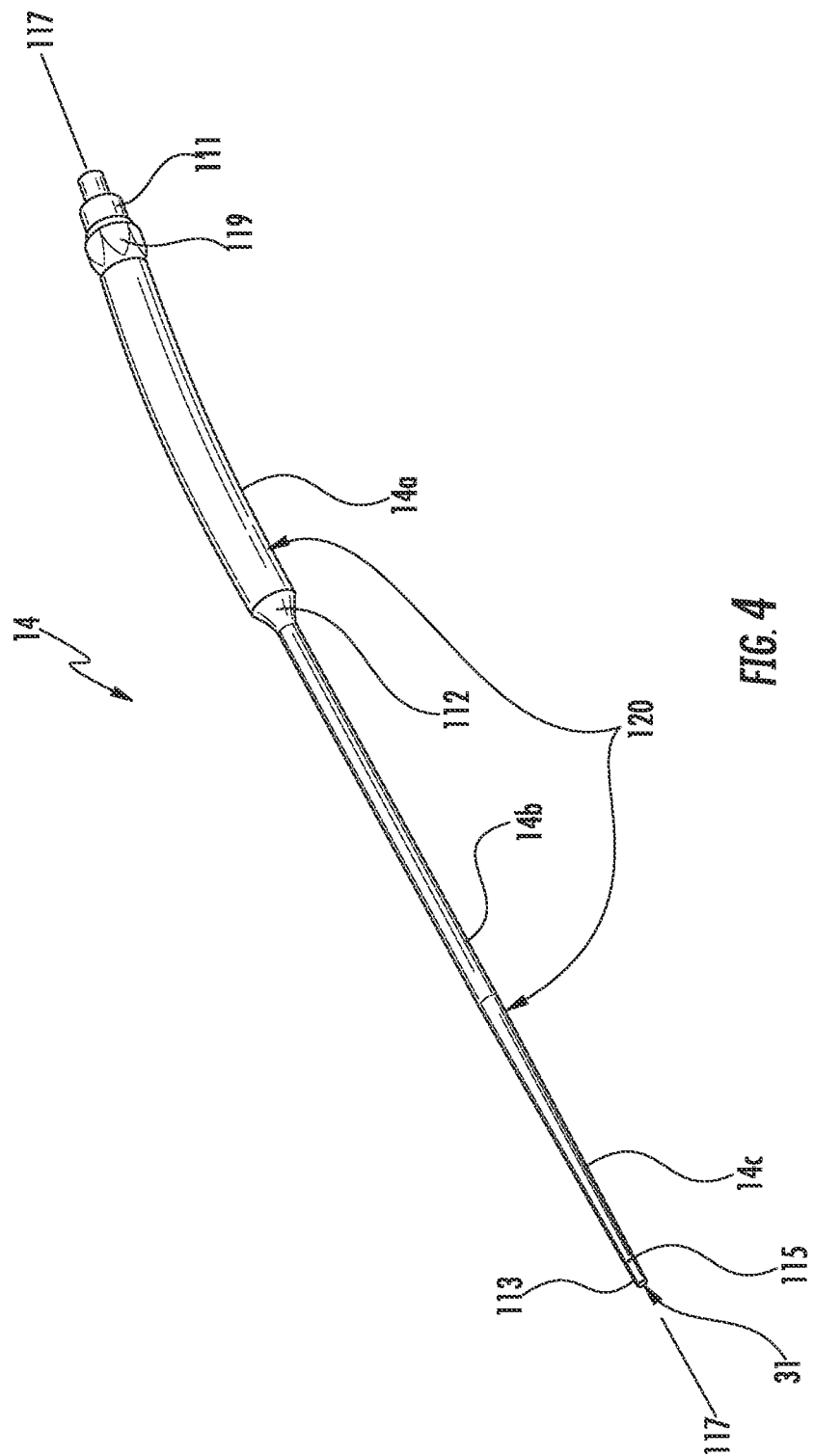
FIG. 4 is a perspective view of an ultrasonic horn.
Figure 5A:
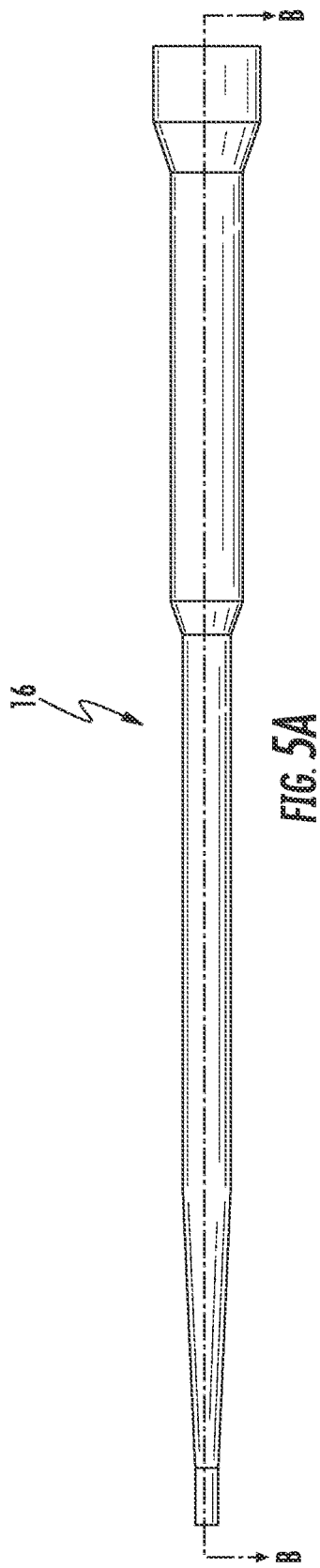
FIG. 5A illustrates a flue in accordance with the present invention.
Figure 5B:
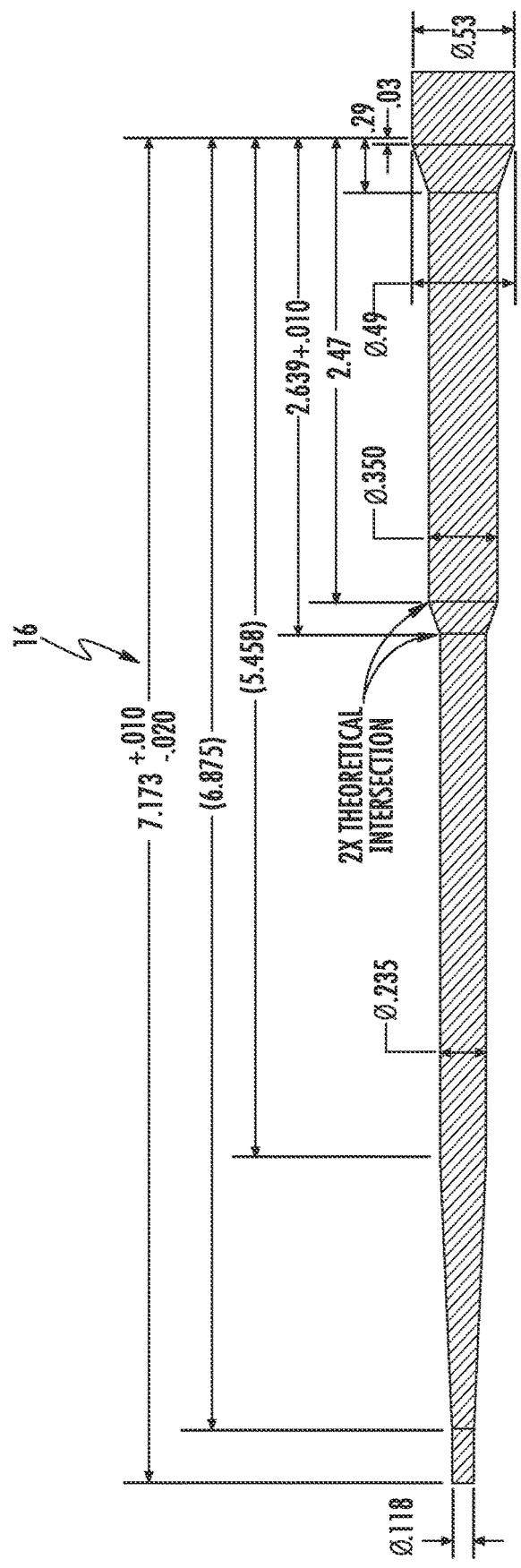
FIG. 5B indicates certain measurements (in inches) of the flue of FIG. 5A.

FIG. 4 illustrates an ultrasonic horn 14, which is suitable for use with the above-described ultrasonic surgical apparatus for fragmenting and aspirating tissue. The ultrasonic horn has an external surface 120 and includes a first horn extender 14a, a second horn extender 14b extending distally from the first horn extender through a horn extender transition segment 112, and a third horn extender 14c extending distally from the second horn extender. The ultrasonic horn may have additional horn extender or extenders, or have only one or two horn extenders. The ultrasonic horn 14 has a distal end portion 113 and a threaded proximal end 111, a throughbore 117, a preaspiration hole or transverse bore 115, and a hexagon engagement portion 119. The ultrasonic horn has a larger external diameter in the first horn extender 14a section and a smaller external diameter in the second horn extender 14b section.

Although the ultrasonic horn as shown is a stepped horn, it is known that there are ultrasonic horns that are not stepped. For example, the ultrasonic horns can have a single long extender body, rather than two horn extenders of two different diameters, and the single long horn extender can have a constant external diameter throughout its length or have a gradually changing diameter along its length, for example, gradually decreasing in diameter along its length distally. In addition, even though two horn extenders may form a stepped configuration, additional extender or extenders may form additional steps or transition smoothly from another extender without forming any apparent step. The ultrasonic horn may vibrate in the ultrasonic frequency range with a longitudinal amplitude in excess of about 5 mils (0.005 inch) to 14 mils (0.014 inch).

The throughbore 117 may also have a larger diameter section within the first horn extender 14a and a smaller diameter section within the second horn extender 14b section. The diameters of the proximal larger diameter and the distal smaller diameter portions of the throughbore may have any suitable diameters as can be readily determined as appropriate by those skilled in the art. For example, the distal smaller diameter throughbore portion may be about 0.045 inches in diameter. The throughbore does not necessarily have to correspond to the geometry of the ultrasonic horn extender or extenders. The throughbore may have two or more diameters in a stepped fashion or otherwise, a constant diameter throughout its length, or a gradually changing (for example, decreasing) diameter along its length distally.

The ultrasonic horn 14 is substantially circular and disposed within the flue 16. During operation of the ultrasonic apparatus 10, irrigation fluid is supplied through the opening 17 into the flue 16. Flue 16 and the ultrasonic horn 14 define an annular cavity 36 therebetween. Irrigation fluid is supplied from flue 16 through cavity 36 to the distal end of the ultrasonic horn 14. A transverse bore is formed in preaspiration holes 115 near the distal end of the ultrasonic horn 14 and communicates with the throughbore 117. The irrigation fluid is drawn from preaspiration holes 115 and the surgical site into inlet 31 of the throughbore 117 along with fragmented tissue, blood, etc., and is removed from the surgical site via the throughbore 117 and the aspiration tube 24. The transverse bore provides an alternate route for fluid to enter throughbore 117 when inlet 31 becomes clogged.

In a more detailed aspect, irrigation liquid, for example saline, is necessary to cool the surgical tip and site of tissue fragmentation. This irrigation liquid is provided to the flue with a peristaltic pump at a rate as low as 2 to 3 ml/min, which is typically only about a drip or two a second. The irrigation liquid is supplied at the proximal end of the ultrasonic horn. The irrigation liquid progresses to near the distal end of the ultrasonic horn, where two preaspiration holes of 0.015 inch diameter suction a majority, perhaps 90-95%, of the irrigation through the holes connecting the outside horn diameter to the central suction channel. This action of irrigation and suction supports a contiguous cooling circuit for the vibrating titanium metal and it also helps to wet effluent such as blood and tissue in the central channel. Some irrigation is also favorable to cooling the surgical site, improving coupling to tissue, and affording cavitation necessary to emulsification and aspiration of tissue, such as tumors.

Referring now to FIGS. 5A, 5B, 6A and 6B, an exemplary embodiment of the present invention is shown. The flue 16 is for use with an ultrasonic horn having an internal surface and an external surface and comprising a first horn extender and a second horn extender extending distally from the first horn extender and having a diameter smaller than the diameter of the first horn extender. The flue has an internal surface 51, an external surface 52, a proximal end 53 and distal end 54 and comprises a first flue extender 16a and a second flue extender 16b extending distally from the first flue extender and having a diameter smaller than the diameter of the first flue extender. The flue additionally has a third flue extender 16c. The first and second flue extenders are configured to at least partially encase or surround the first and second horn extenders.

Figure 7A:
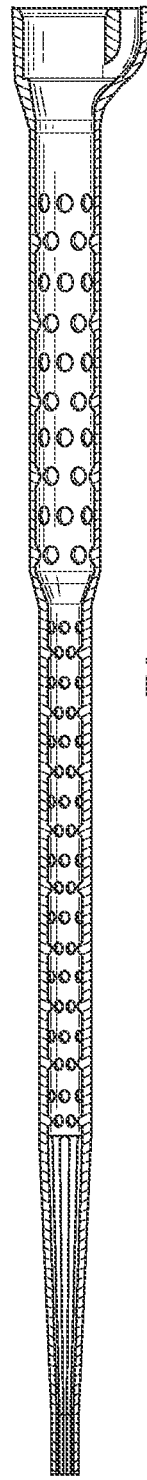
FIG. 7A is another illustration of the flue of FIG. 5A.
Figure 7B:
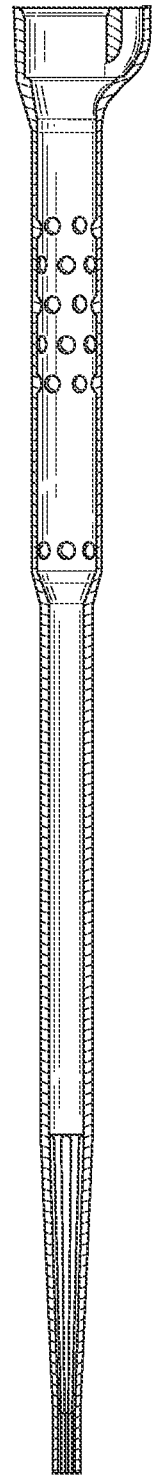
FIG. 7B illustrates a currently marketed flue.
Figure 8A:
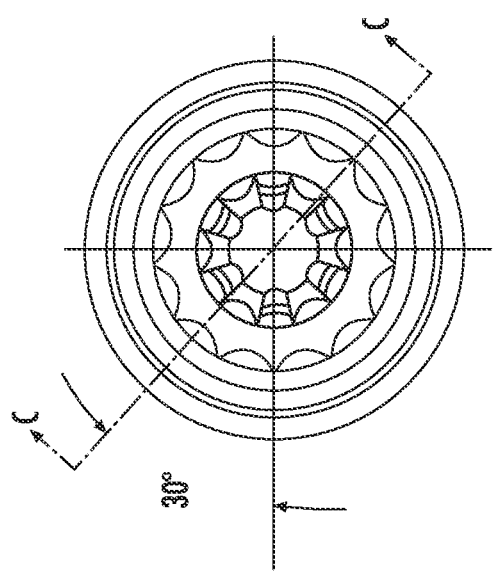
FIGS. 8A and 8B show a cross-sectional view of the flue of FIG. 5A taken from a different angle rotated about the longitudinal axis L.
Figure 8B:
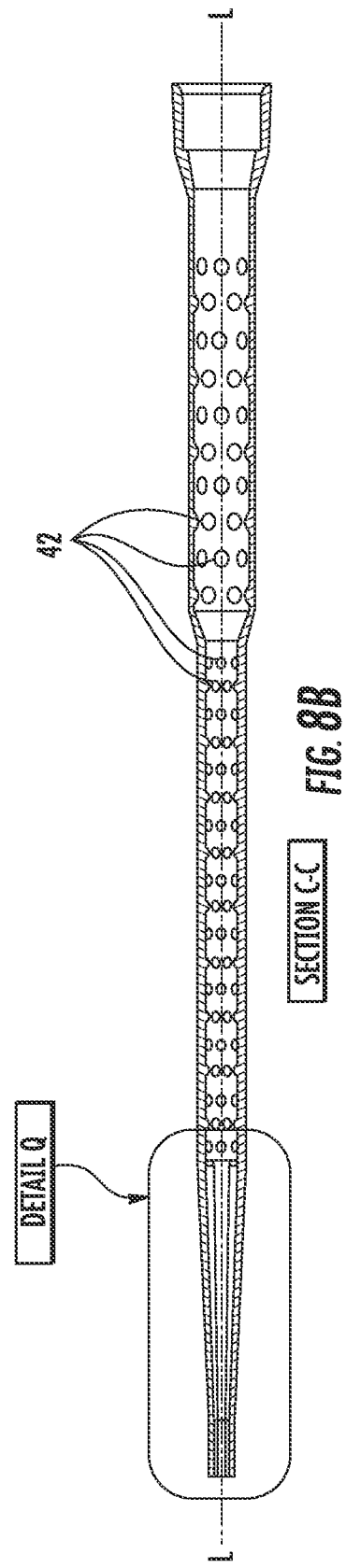
Figure 9:
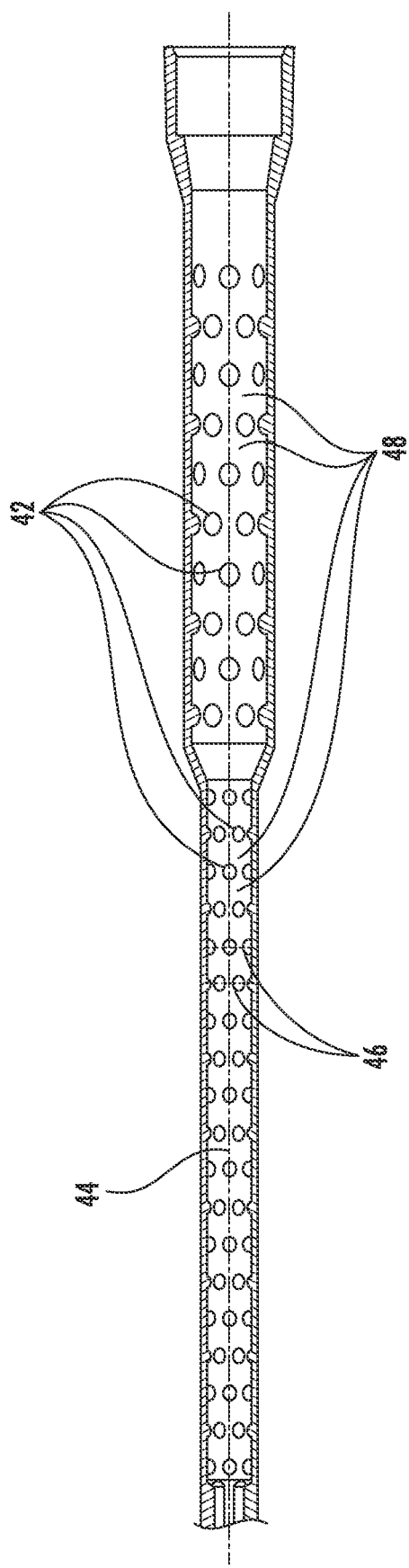
FIG. 9 is an enlarged view of a section of the flue of FIG. 8B showing longitudinal and axial bridges.
Figure 10:
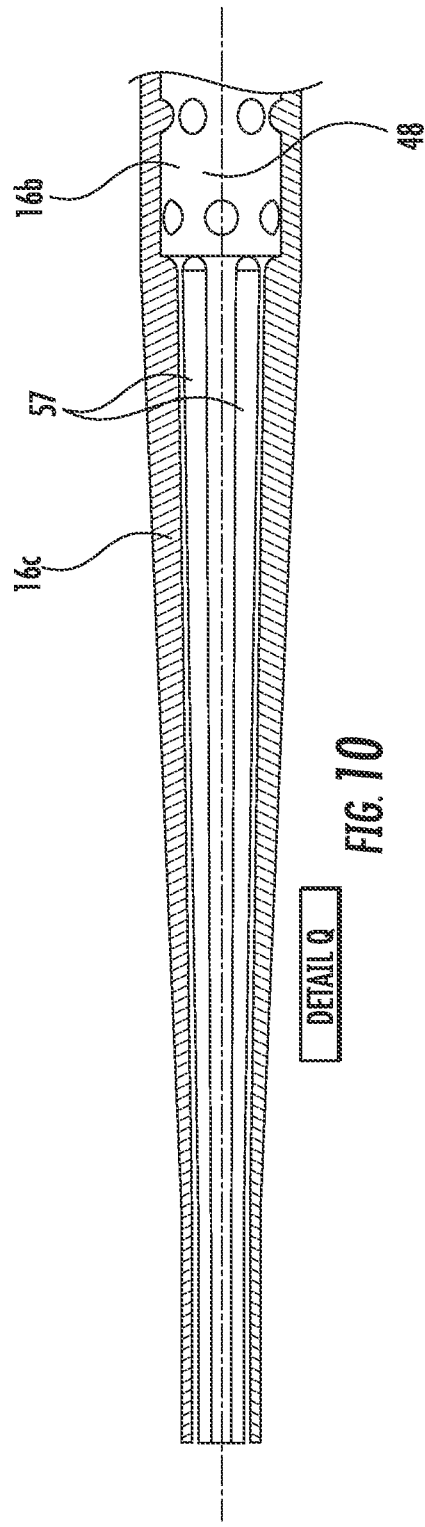
FIG. 10 is a detailed illustration of a section of the view of FIG. 8B.
Figure 13:
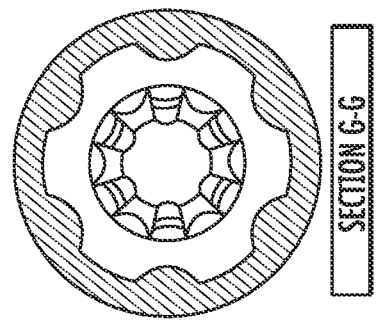
FIG. 13 is a cross-sectional view taken at section line G-G of FIG. 6A.
Figure 12:
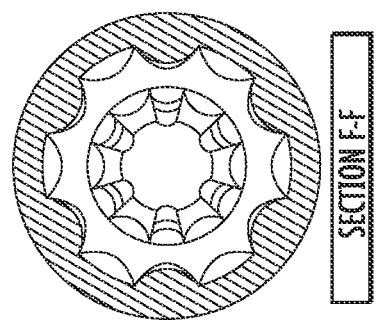
FIG. 12 is a cross-sectional view taken at section line F-F of FIG. 6A.
Figure 11:
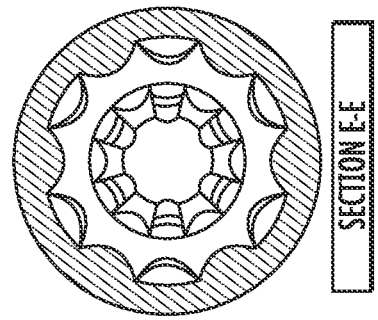
FIG. 11 is a cross-sectional view taken at section line E-E of FIG. 6A.
Figure 16:
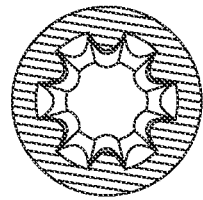
FIG. 16 is a cross-sectional view taken at section line N-N of FIG. 6A.
Figure 15:
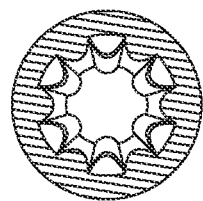
FIG. 15 is a cross-sectional view taken at section line M-M of FIG. 6A.
Figure 14:
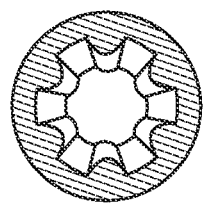
FIG. 14 is a cross-sectional view taken at section line H-H of FIG. 6A.

FIG. 7A is another illustration of the flue 16 in accordance with the present invention, and FIG. 7B shows a prior art device. As shown in FIG. 7B, the existing flues on the market have sparse protrusion about the antinode, and near the node at the end of the surgical tip extender. This surgical tip utilizes a 60 durometer flexible silicone flue. The protrusions are located only over the large flue extender. The existing devices have protrusions only at the high motion lower-strain regions and are inadequate for protecting tissue external to the flue. For example, CUSA® Excel Extended MicroTip Plus (EMT+) surgical tip (Integra LifeSciences Corporation, Plainsboro, NJ) and other CUSA Excel surgical tips employ silicone flues that do not utilize protrusions at high strain areas. Also, the sparse protrusions can be spread under moderate loading on existing flues. Many existing extended surgical tips have protrusions on the internal diameter of their flues but only about the antinode, or point of greatest motion, of their horn extenders.

As discussed earlier, a flue is often employed to deliver irrigation liquid and it protects tissue along the path to the surgical site from the vibrating surgical tip. The transducer vibrates along its length and stepped horns and specialty profiles of reduced diameter amplify vibration. It has been found in practice that sometimes a surgeon will compress the flue to tissue under high loading during vibration of the surgical tip causing thermal rise that can burn tissue. A surgical tip having a second horn extender of one-half wavelength which is of smaller diameter has greater motion than the large first horn extender due to greater mechanical gain. Compression of the flue to the vibrating surgical tip could cause thermal rise and thus has potential to create burns to the patient. Metal work heating may be experienced due to strain by bending a thin piece of metal or wire rod until it gets hot or until it breaks. The causes of such thermal rise have been identified, and the flues of the present invention address the identified issues to prevent such thermal rise.

Turning now to FIGS. 8A, 8B and 9-18, the internal surface 51 of the second flue extender comprises a planar region 48 (that is planar as shown in the cross-sectional view of FIGS. 8A-8B, 9, and 10), or region between protrusions, and a plurality of protrusions 42 forming bridges 44, 46 that limits contact between the planar region 48 of the internal surface of second flue extender and the external surface of the second horn extender. It should be understood that the region 48 between the protrusions and/or inwardly projecting protrusions 42 of the internal surface 51 in a perspective view are generally cylindrical about the longitudinal axis L and may be a variety of shapes, sizes, relative positions, construction, and quantities and still be within the scope of the invention. In the embodiments shown, the region 48 between protrusions 42 is arcuate. However it should be understood that the region 48 may be a variety of shapes or contours.

In another aspect of the present invention, the protrusions are distributed at locations that correspond to locations on or near or about a node of the ultrasonic horn, on the first horn extender, the second horn extender and/or any additional horn extenders. The ultrasonic wave generated by the resonator has at least one node and at least one antinode. An antinode is a point of maximum displacement and a node is a point of minimum displacement in the wave. The protrusions form one or more bridges that limit contact between the planar region of the internal surface of the flue and the external surface of the ultrasonic horn. The flue may further comprise protrusions on its internal surface at locations that correspond to locations on or near or about an antinode of the ultrasonic horn, and/or at locations that correspond to locations of high strain gradient and motion, such as between nodes and antinodes of the ultrasonic horn.

Preferably at least a portion of the internal surface of the second flue extender has protrusions. The internal surface may have at least 3 protrusions per square centimeter and preferably at least 5 protrusions per square centimeter. The protrusions may be present beyond the locations that correspond to the locations on or about one or more antinodes or beyond the greatest motion point on the ultrasonic horn, and preferably on substantially the entire internal surface of the flue corresponding to one or more horn extenders, for example, on the entire surface of the second flue extender, the entire surface of the first flue extender, and/or additional the entire surface of any additional flue extender(s). In a flue that has first and second flue extenders, the large flue extender has at least 3 protrusions per square centimeter and the small flue extender has at least 5 protrusions per square centimeter. The protrusions are preferably present on the smaller flue extender in a higher density than those on the larger flue extender, but the protrusions on the smaller flue extender may be in the same density as those on the larger flue extender or even lower in density than those on the larger flue extender although it would seem unusual to have a lower density of protrusions on the small diameter flue extender than the larger diameter flue extender, as gain, strain, and motion is greater for the smaller flue extender of the horn.

Flue 16 supplies irrigation fluid to an operative site during surgery. Since flue 16 is a hollow member, protrusions 42 are included for strength and may contact the ultrasonic horn. Protrusions 42 help maintain flue 16 and ultrasonic horn concentricity. The ultrasonic horn has a second horn extender of one-half wavelength which is of smaller diameter and has greater motion than the large first horn extender due to greater mechanical gain. The pattern, density, and region of protrusions have been improved. Protrusions are added as molded bumps to the second flue extender portion that corresponds to the second horn extender portion. Additionally, it has been learned that vibrational heating could occur at other high strain areas beyond the antinode, so the area with protrusions has been extended. Finally, it has been learned that protrusions in simple rows could be separated by compressing the flue with point or line loading, such that they spread and allow the thin wall of the silicone flue to compress to the vibrating tip. Consequently, the protrusions have been placed in a more complex pattern of greater density to aid in providing bridges to resist compression of the thin wall of the flue while allowing irrigation liquid to continue to flow beneath the bridges. Changing the complexity of the pattern, density and force needed to compress protrusions, and extending the region of protection of protrusions can greatly reduce thermal rise in compression, thereby reducing likelihood of burns of adjacent tissue protected by the flue. The pattern and density of protrusions have been improved, such that bridges are formed and sustained under high loads which keep the thin wall of the silicone flue from contacting the vibrating horn, and these bridges allow irrigation liquid to continue to flow.

The flue has generally the same shape as the ultrasonic horn with which the flue is used and is configured to position about the external surface of the ultrasonic horn, which may have no step or have one or more steps. Although it is shown that two flue extenders of different internal diameters form a stepped configuration, additional flue extender or extenders may form additional steps or transition smoothly from another extender without forming any apparent step.

A flue may be provided for use with an ultrasonic horn that does not have stepped diameters. For example, the flue may have a single elongated flue extender body, rather than two or more distinct flue extenders of two different diameters, and the single elongated flue extender may have a constant diameter throughout its length or have a gradually changing diameter along its length, for example, gradually decreasing in diameter along its length distally. In that case, the term "flue extender" may refer to a flue extender section of the elongated extender body, and the term "flue extenders" may refer to two or more flue extender sections that may not have any distinct transition point.

The third flue extender 16c has six ribs 57 on the internal wall of the flue 16. The ribs 57 provide structural integrity to this section of the flue and allow it to be inserted around the surgical tip and allowing irrigation fluid to flow around the surgical tip to the distal end portion of the surgical tip.

Figure 19:
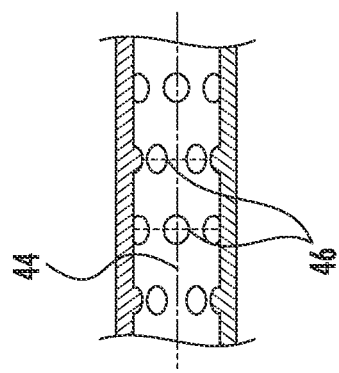
FIG. 19 illustrates the formation of bridges both longitudinally and axially by protrusions.

As shown in FIG. 19, bridges 44, 46 are formed by the protrusions. Under even a point load of the thin wall of the silicone, the cylindrical surgical tip surface engages protrusions both longitudinally and axillary. The protrusions are distributed in staggered rows and columns such that one protrusion is centered about every four adjacent protrusions arranged in a substantially square or rectangular manner. The protrusions form longitudinal bridges 44 and also axial bridges 46. The cylindrical surface cannot fit between and spread the protrusions without causing increasing resistance and distribution of loading. Irrigation liquid can continue to find circuits under the multi-axis bridges.

The protrusions on the flue may be in the form of spheres. In the embodiment shown in FIG. 6B, the spherical radius of the protrusions on the first, larger flue extender is about 0.047 inches, and the spherical radius of the protrusions on the second, smaller flue extender is about 0.028 inches. In this embodiment, the spherical protrusions on the first flue extender all have the same size and the spherical protrusions on the second flue extender all have the same size, and the spherical protrusions of the first flue extender are larger than those on the second flue extender. The spheres may have different sizes than those shown in the exemplary embodiment, at least partly depending on the size of the ultrasonic horn and the designed strength of the flue. The spherical radius of the protrusions on the first, larger flue extender may be in the range of about 0.01 to about 0.10 inches, or about 0.02 to about 0.08 inches, and the spherical radius of the protrusions on the second, smaller flue extender may be in the range of about 0.01 to about 0.08 inches, or about 0.01 to about 0.05 inches.

In the embodiment as shown in the drawings, there are 6 spherical protrusions in each row about the longitudinal axis. The protrusions on the first flue extender are all identical in shape and size in this embodiment, but they do not need to be identical. Likewise, the protrusions on the second flue extender are all identical in shape and size, but they do not need to be identical. The protrusions on the larger flue extender are preferably generally larger than those on the smaller flue extender, but the protrusions on the larger flue extender may be of the same size as those on the smaller flue extender or smaller than those on the smaller flue extender.

Stated in another way, the protrusions may have an average spherical diameter of about 0.02 to about 0.14 (about 0.5 mm to about 3.5 mm), preferably about 0.04 to about 0.12 inches (about 1.0 mm to about 3.0 mm). In the above mentioned embodiment that has first and second horn extenders, the protrusions on the larger flue extender may have an average diameter of about 0.09 to about 0.10 inches (about 2.2 mm to about 2.6 mm), and the protrusions on the smaller flue extender may have an average diameter of about 0.05 to about 0.06 inches (about 1.2 mm to about 1.6 mm).

The protrusions do not need to be in spherical form as shown and may have any suitable shapes and dimensions. The protrusions may have an average height in the range of about 0.01 to about 0.10 inches, about 0.01 to about 0.06 inches (about 0.2 mm to about 1.5 mm), or about 0.01 to about 0.04 inches (about 0.2 mm to about 1.0 mm). For example, in an embodiment of an flue for use with a stepped ultrasonic horn comprising a larger first horn extender and a smaller second horn extender, the protrusions on the large flue extender may have an average height of 0.02 to about 0.06 inches (about 0.5 to about 1.5 mm) and those on the small flue extender may have an average height of 0.01 to about 0.03 inches (about 0.2 mm to about 0.8 mm).

As stated earlier, although the flue has been shown and described to have circular cross-sections, it is understood that the protrusions do not have to have generally cylindrical or circular in cross-sections. The protrusions can be in any suitable geometry without departing from the spirit of the present invention. In addition, the height, diameter and/or density of the protrusions do not have to be consistent across the entire internal surface of the flue or across the internal surface of a flue extender or any regions thereof.

It has been determined with visible observation and physical temperature monitoring that high loading of the flue could spread the protrusions such that the thin walled silicone could contact the surgical tip. This is dependent on the density of the protrusions, radius of the tip, force and point or line load applied, and secondarily on the durometer of the rubber flue. Increasing the density of the protrusions provides resistance to a distributed load, essentially, dividing the load by number of protrusions supporting the load. The protrusions form bridges to even a point load to provide a degree of resistance to the thin wall contacting the vibrating tip. This is one of the reasons the friction and heating increase with point loading and magnitude of point loading forces. It has been learned that a reasonable and excessive load could be supported with improved temperatures monitored due to reduced heating. The bridges formed by the protrusions, even under compression of the flue, enable a path for irrigation liquid: it flows under the bridges. The density of protrusion can be increased to better support the smaller radius of the small flue extender, and the pattern can be adjusted to provide bridges both longitudinally and axially.

Figure 20:
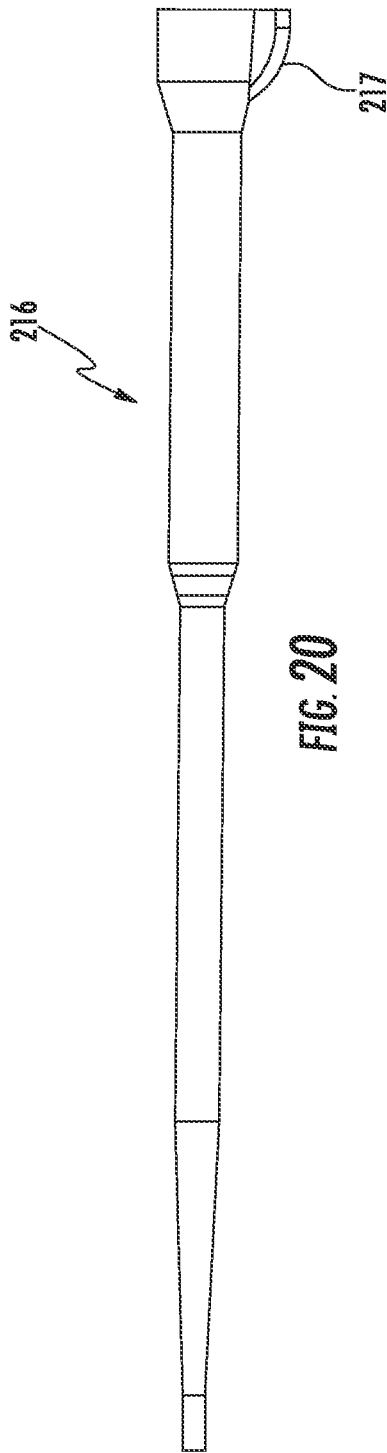
FIG. 20 illustrates another embodiment of the flue in accordance with the present invention.
Figure 21:
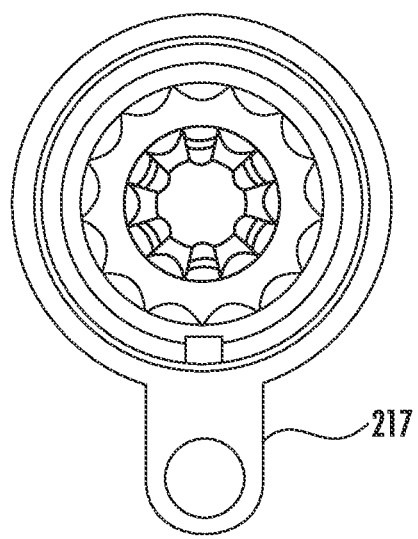
FIG. 21 is a proximal end view of the flue of FIG. 20.

FIGS. 20 and 21 show another embodiment of a flue 216 in accordance with the present invention. The flue has a flue tube connection section 217. As shown in FIG. 22, the flue connects to a flue tube 218 at the flue tube connection section 217, for example, by molding or other methods known in the art. The flue tube 218 has a Luer fitting 211 for connection with an irrigation tube 22.

The flue can be made of silicone, other elastomer or other suitable material. The flue tube can be made of silicone, other elastomer or other suitable material that is the same or different from the material of the flue. For example, a thin walled silicone flue of about 0.01 to 0.05 inches in thickness may be used. A preferred material is silicone, such as silicone rubber compounds from Dow Corning. Silicone maintains integrity under catastrophic conditions such as loss of irrigation or clogging of the surgical tip. It is known that even traction or loading alone can damage nerves, and the silicone rubber provides some cushion relative to rigid flues. Silicone is rubber, and this material damps ultrasound that could propagate from the surgical tip to critical anatomy. Silicone, such as 60 Durometers, is flexible and conforms to curved surgical tips that provide clinical benefit in increased visualization under the surgeon's microscope. Other suitable materials known to those skilled in art may also be used to make the flue.

Rigid flues made of materials such as polymethylpentene (PMP), acetal homopolymer resin (such as DuPont® Delrin® material), and polytetrafluoroethylene (PTFE) are also contemplated. However, rigid flues may experience problems such as cracking and melting under catastrophic circumstances, such as loss of irrigation or surgical tip clogging. Rigid flues, for example flues made of hard polymers, may be more effective in distributing contact forces, thereby reducing concentrated frictional heating. The added stiffness from the increased durometer may help distribute the load more evenly, and therefore reduce the heating. It is also clear that rigid flues extend the useful range of surgical tips, such that the surgeon can steady or grip the flue of a longer surgical tip. However, rigid flues may not be suitable for curved tips, as the clearances and bend angles that would be needed obstruct the surgeon's line-of-sight to the distal end of the tip and surgical site. A flexible silicone material works better for these tips because it easily conforms to the shape of the tip and fits tightly against the tip, reducing the bulk of the design and providing the surgeon with a much better line-of-sight. Similarly, the internal bumps also might help distribute the load more evenly to reduce heating while simultaneously creating a more uniform irrigation flow to help sink heat away.

The flues in accordance with the present invention can be made by molding or other conventional manufacturing methods. The flues can be used with the existing ultrasonic surgical tips, such as CUSA Excel surgical tips, CUSA NXT 35 kHz extended length tip, or other ultrasonic surgical aspiration instruments on the market or being developed. The surgical tips may be straight or curved, and may have different lengths or tip designs. In terms of applications, the ultrasonic surgical apparatus comprising an ultrasonic horn and a flue in accordance with the present invention is useful for known applications of ultrasonic aspirators such as cranial-based surgery and when performing transsphenoidal or endoscopic-nasal approaches.

Thermal data showed that the hot spot or maximum temperature was beyond the antinode of the small horn extender (second horn extender) of the EMT Plus flue. The most problematic area along the length of the tip in terms of heating due to lateral loading is located along the small horn extender where there are currently no additional safety considerations built into the design. This is where the motion and the maximum strain gradient contribute to heating.

Silicon flues were prototyped and tested in engineering bench studies and at a cadaver lab. Quantitative assessment in these studies shows the measureable improvement in reduce temperature under nominal, high, and excessive loading.

Example 1. Motion of Ultrasonic Horn

The EMT Plus flue has a first horn extender, a second horn extender and a third horn extender. In the description of the testing and results in the EXAMPLES, the second horn extender is referred to herein as an added horn extender or added extender, and the first horn extender is referred to as a conventional horn extender or a conventional extender.

Figure 23A:
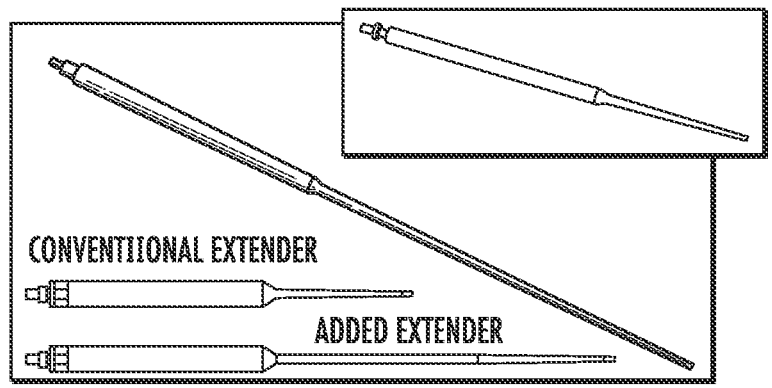
FIGS. 23A, 23B, and 23C illustrate maximum displacement regions of a surgical tip that has three extenders.
Figure 23B:
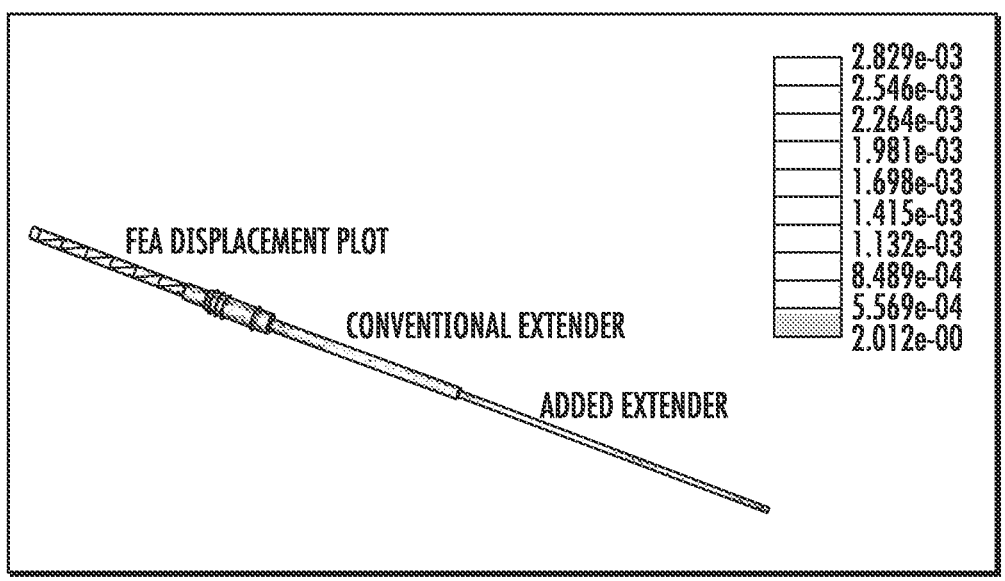
Figure 23C:
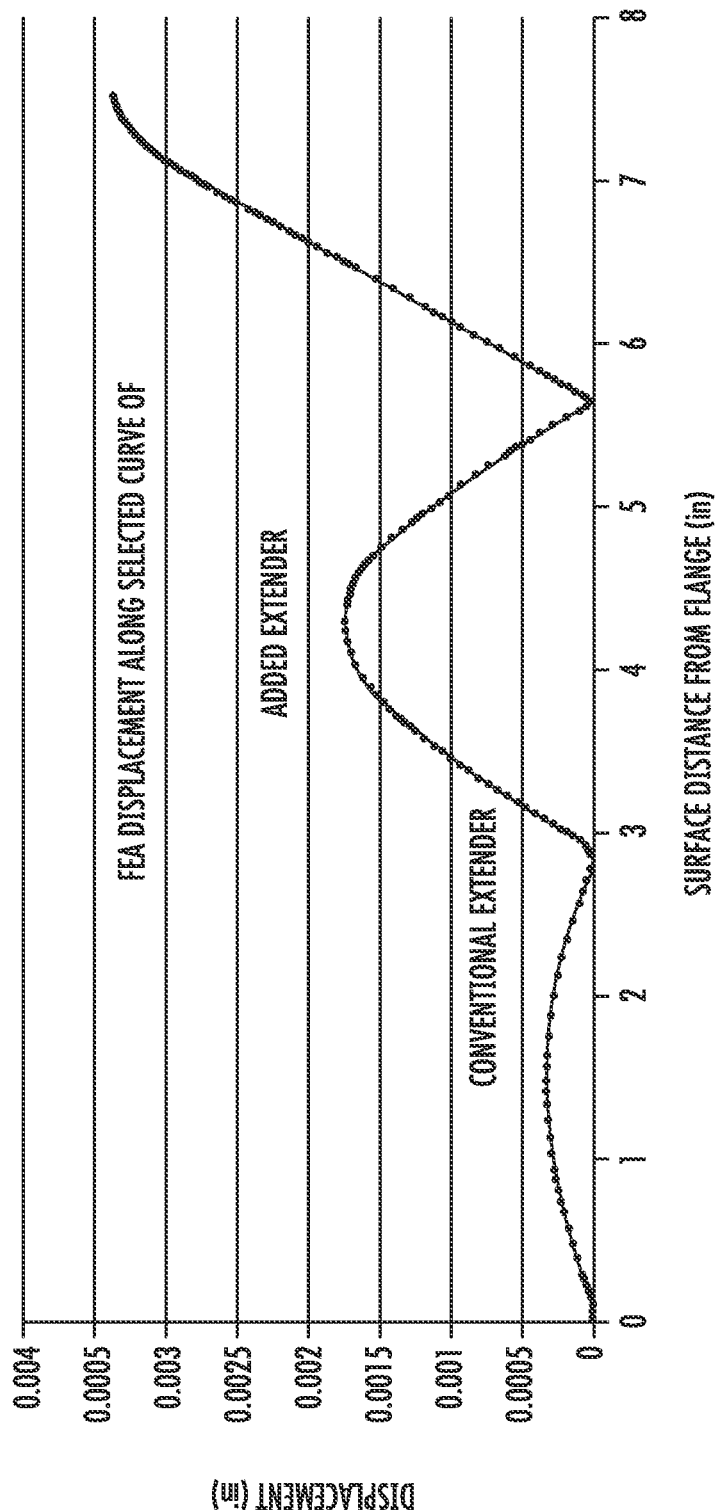

Motion is modeled with Finite Element Analysis (FEA) and the results are shown in FIGS. 23A-C. The added extender has about 4 times the motion of the conventional extender.

Example 2. Determination of High Strain Regions on Ultrasonic Horn

The discovery of the heating at high strain areas came about in probing for "hot spots" along the surgical tip and compressed flue. Amplitude of a surgical tip is accomplished with strain. The displacement or elongation of a spring provides an analogy to the ultrasonic horn, where the motion at the end of the horn is due to stretch of the metal of the horn, instead of the spring, physically. Elongation is the integral of strain along the length of the horn, given by change in length is equal to change in length/length times total length as shown in equation (1) below.

$$\varepsilon = \epsilon L = \left(\frac{\Delta L}{L}\right) L, \text{ where } \varepsilon \text{ is elongation, } \epsilon \text{ is strain, and } L \text{ is length.} \quad (1)$$

Particle friction from the bending strain heats the metal, and it can fatigue. Titanium, such as used in ultrasonic horns and aircraft, can withstand very high fatigue or cycling rates without breaking. Contacting regions of high strain with particle motion at ultrasonic frequencies, of say 25-50 kHz or 25,000 to 50,000 cycles per second, an extreme form of stretching on bending, can cause heating and conduct heat to the stationary flue.

Figure 24:
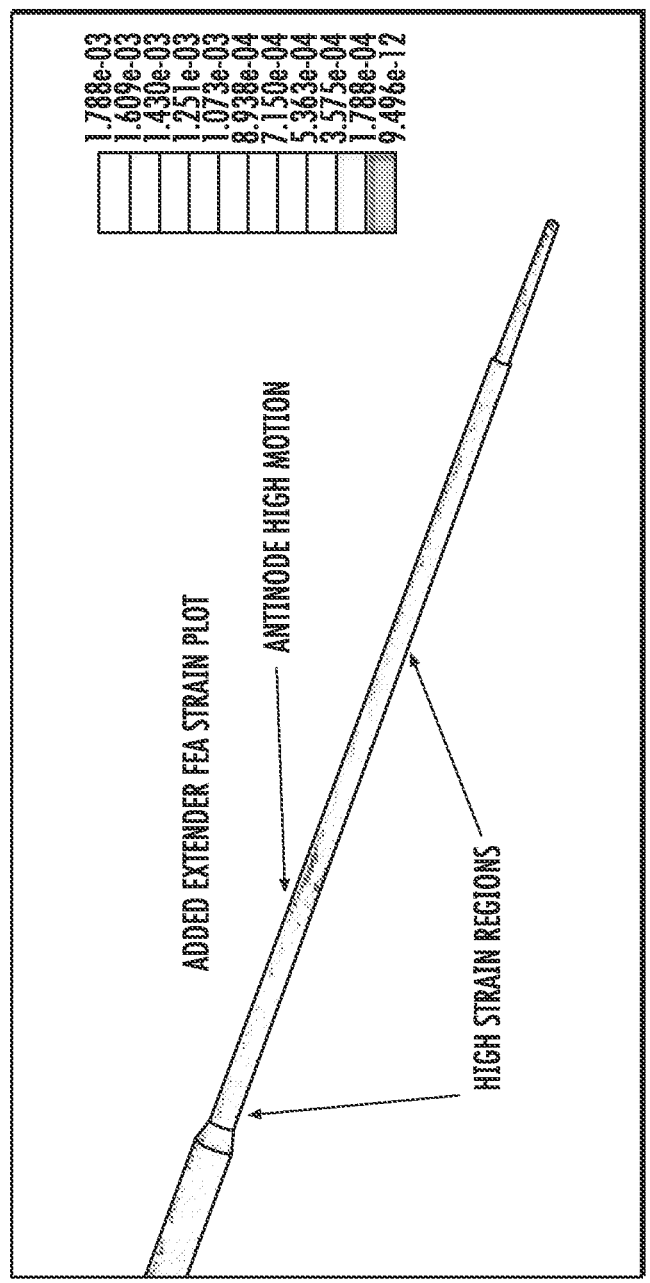
FIG. 24 a schematic diagram showing strain regions.

High strain regions for EMT Plus are shown with FEA in FIG. 24. It becomes clear the prior art devices where the protrusions are only at the high motion lower-strain regions are inadequate for protecting tissue external to the flue, if the flue is compressed to high strain regions. FEA reveals high strain regions. It was determine that elevated temperatures known to occur at motion maximum regions, or about antinodes, could also occur under flue compression to areas of high strain, particle motion.

Example 3. Flue for Extended MicroTip Plus

Changes were made to the Extended MicroTip Plus (EMT+) flue to address issues of high temperatures due to compression on the flue to the horn extenders. Some locations of these potential complications have been associated with the small extender in endonasal approaches. Protrusions were extended to larger areas, not only at motion maximum regions or about antinodes, but also at areas of high strain, particle motion.

The new EMT+ flue was molded in Dow Corning Class VI Liquid Silicone Rubber Elastomer C6-560. This material is heat stable to 204° C., can be autoclaved, and has a tensile strength of 8.55 MPa after 8 hour post cure. The durometer hardness, Shore A, after post cure is 60. Its tear strength is 50.7 kN/m after post cure.

Example 4. Cadaver Lab Testing

In the cadaver lab, the surgeon was asked to feel the achievable forces in the nasal passage, when constrained by the anatomy over the length of the Curved Extended Micro-Tip Plus and its flue. The surgeon was asked to force the handpiece and surgical tip outside of the cadaver with a load cell placed directly at the antinode of the small diameter extender, such that the force could be assessed corresponding to the surgeon's feel in the cadaver nasal passage. The surgeon was asked to load the flue and surgical tip to the degree expected in the nasal passage, even a maximum load. Then, the surgeon was asked to exert a force they felt was clearly excessive, such that this lateral load would not be expected.

Figure 25:
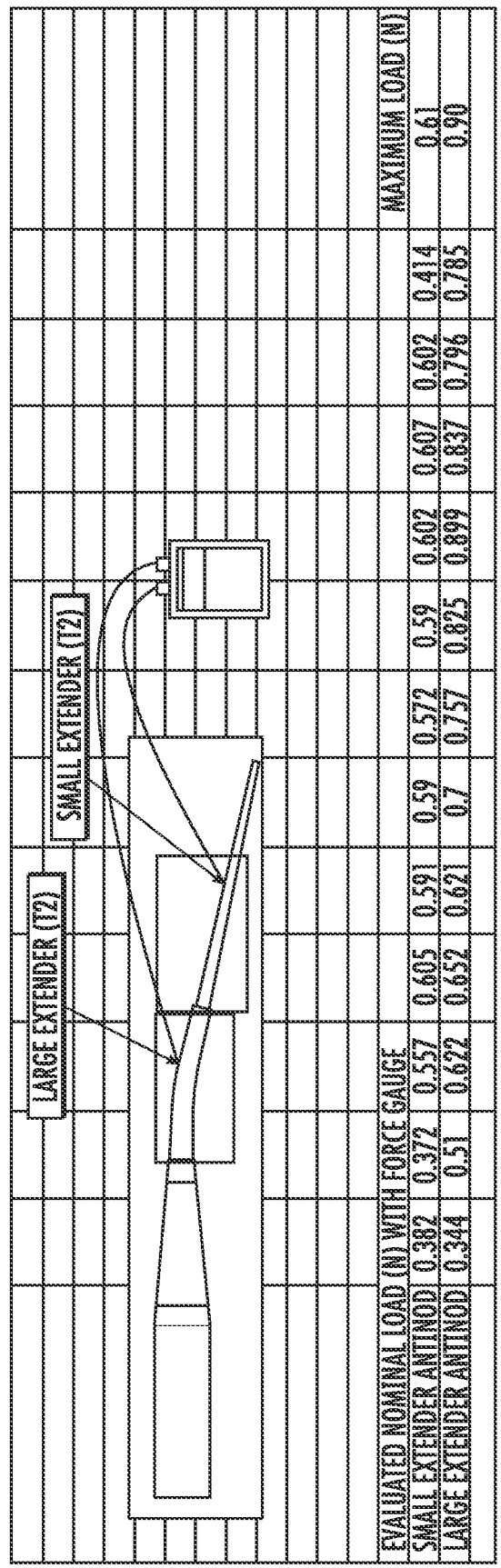
FIGS. 25 and 26 show quantification of excessive lateral loading.
Figure 26:
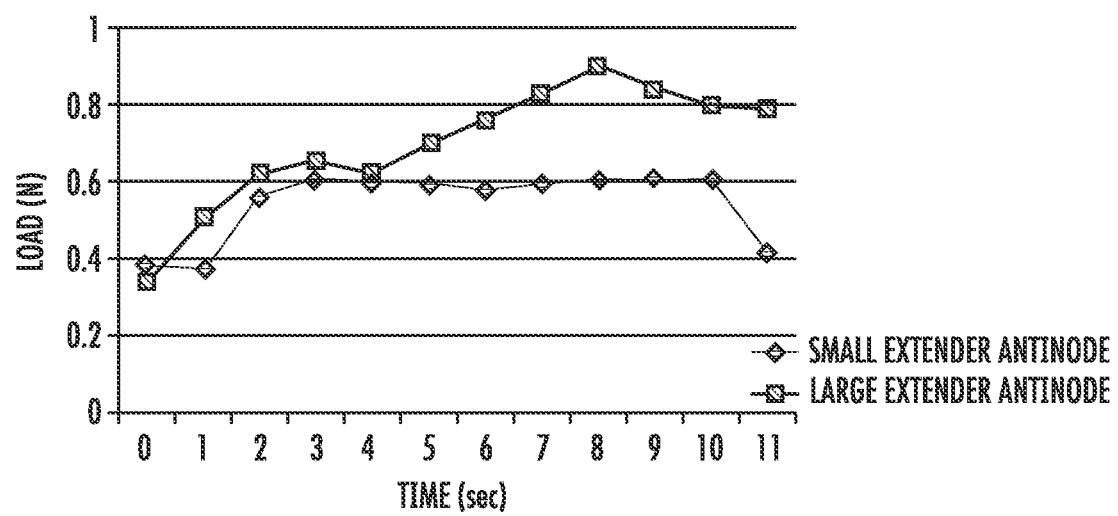

The surgeon believed a force that could be achieved at the small extender but was significantly higher than he would use was 0.6 N. About a 0.9 N force was quantified similarly at the large horn extender. The surgeon felt it was unlikely loading would be higher than these levels, and he was straining somewhat to achieve any load higher in force. Thermal data were then acquired in the cadaver section, with a thermal couple adhered to the flue and compressed against the turbinate in the nasal passage. The surgeon maintained the load only until the local maximum temperature was achieved, as they were exerting themselves. FIGS. 25 and 26 show the normal load measured at different location on the tip under different forces.

Figure 27A:
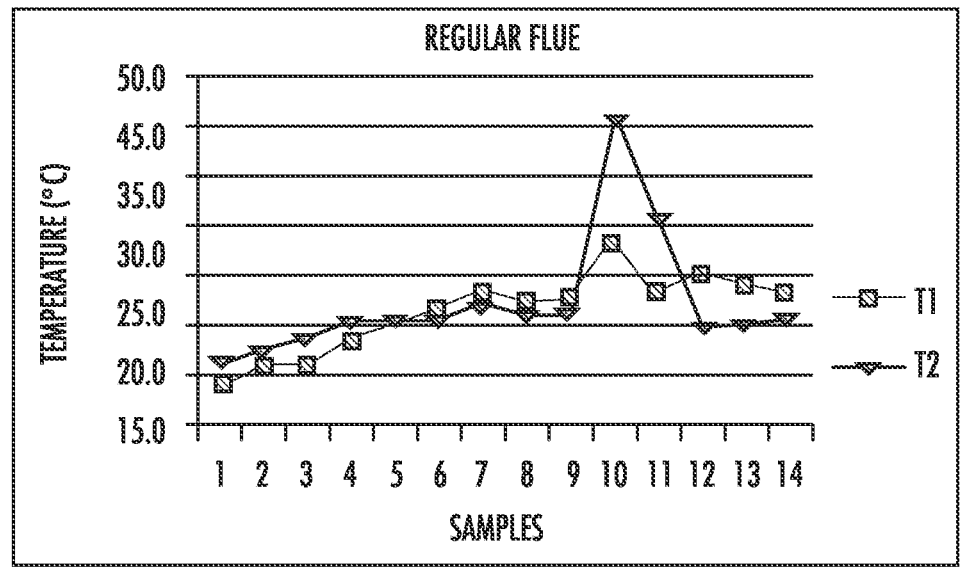
FIG. 27A shows cadaver thermal data of the baseline flue.
Figure 27B:
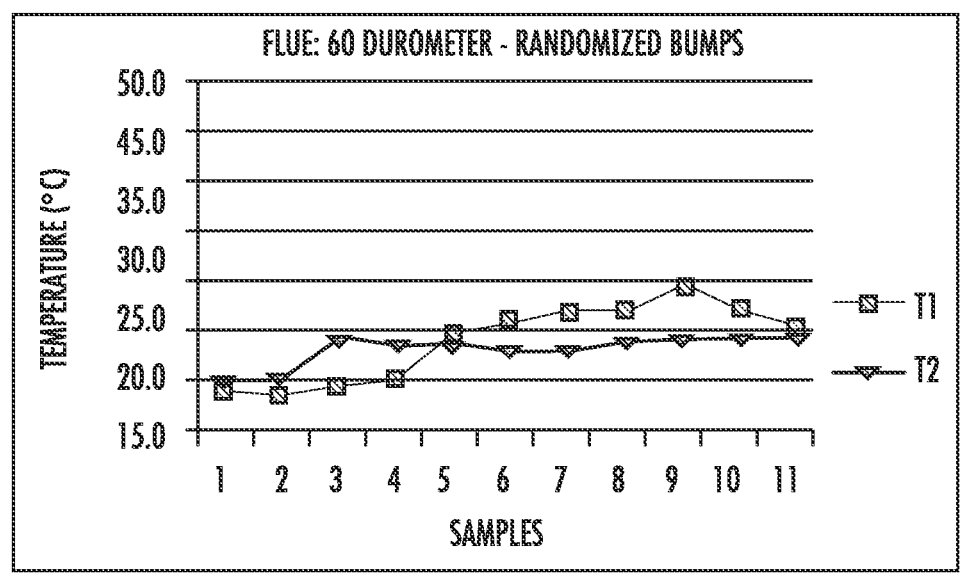
FIG. 27B shows cadaver thermal data of an embodiment of the flue in accordance with the present invention.

Data were acquired at two locations about antinodes of the extenders of the surgical tip and flue, as recorded in Table 1 and Table 2, and plotted in the charts of FIGS. 27A and 27B, respectively.

TABLE 1

Thermal Data with Baseline Flue

| Regular 60 durometer 35 kHz Extended Length | Thermocouple Temperature (° C.) | | Thermocouple Temperature (° C.) | |
|---|---|---|---|---|
| Baseline Flue from Vesta | T1 | T2 | T1 | T2 |
| Note: Nominal to High Loading | 19.0 | 21.0 | 27.2 | 25.8 |
| | 20.9 | 22.5 | 27.3 | 26.0 |
| | 21.0 | 23.8 | 33.3 | 45.7 |
| | 23.7 | 25.2 | 28.5 | 35.5 |
| | 25.0 | 25.3 | 29.9 | 24.7 |
| | 26.3 | 25.5 | 29.0 | 25.1 |
| | 28.1 | 27.1 | 28.2 | 25.4 |

TABLE 2

Thermal Data with Prototype Flue (according to the present invention)

| 60 Durometer with randomized bumps - 35 kHz | Thermocouple | | Thermocouple | |
|---|---|---|---|---|
| Extended Length Flue | T1 | T2 | T1 | T2 |
| Note: Nominal to High Loading | 19.0 | 20.0 | 27.4 | 23.9 |
| | 18.7 | 20.0 | 29.8 | 24.2 |
| | 19.7 | 24.5 | 27.4 | 24.4 |
| | 19.8 | 24.0 | 25.7 | 24.6 |
| | 25.0 | 23.7 | | |

TABLE 2-continued

Thermal Data with Prototype Flue (according to the present invention)

| 60 Durometer with randomized bumps - 35 kHz | Thermocouple | | Thermocouple | |
|---|---|---|---|---|
| Extended Length Flue | T1 | T2 | T1 | T2 |
| | 26.3 | 22.7 | | |
| | 27.5 | 22.8 | | |

The starting cadaver temperature was 19° C., and maximum temperature of the baseline commercial flue was quantified at 33.3° C. at high load about the antinode of the small extender and 45.7° C. at the high load of the large extender. It should be noted that the large extender would not normally be in the nasal passage in endonasal approaches, but could be inserted in some extended endonasal approaches. In this commercial flue, there were no protrusions in the small extended, and the large extender had lower density of protrusions. The temperature was then monitored with 60 durometer prototype flue with the improved pattern, density, and extended region of protrusions in accordance with the present invention. The nominal to high loading by the surgeon's feel for the improved flue yielded 29.8° C. for the small extender and 24.6° C. for the large extender.

Example 5. Point Load Testing

A variable load apparatus was used in conducting point load tests. The apparatus includes a custom wooden load cell attached. Load cell is normal to the flue surface, and is located at the antinode of the small extender. Thermocouple for temperature measurement is located between the wooden load cell and flue. The test procedure for 60 Durometer 35 kHz ELT Flues (Albright) is as follows: (1) Attach a 35 kHz Neuro test handpiece and 35 kHz Extended Length Test Tip to the CUSA NXT test console. Attach a 35 kHz Extended Length 60 Durometer Flue to the handpiece-tip assembly. (2) Attach a T-type thermocouple to the outside of the flue at the antinode region of the small extender. Attach the custom wooden point load cell to the Chatillon Force Gauge, and load the flue directly over the thermocouple. Ensure that the load cell is normal to the flue surface. (3) Adjust the load of the load cell to 0.6N. Record the starting temperature of the thermocouple. Prime the flue and then run the console at 100% aspiration, 3 mL/min irrigation, and 100% amplitude until the temperature stabilizes. Record this temperature. Repeat this step 5 times, reloading the tip every time. (4) Repeat Step 4.3 with loads of 0.9N and 1.2N. (5) Remove the T-type thermocouple and attach to the outside of the flue at the antinode region of the larger extender. Again load the flue directly over the thermocouple, ensuring that the load cell is normal to the flue surface. (6) Adjust the load cell to 0.9N. Record the starting temperature of the thermocouple. Prime the flue and then run the console at 100% aspiration, 3 mL/min irrigation, and 100% amplitude until the temperature stabilizes. Record this temperature. Repeat this step 5 times, reloading the tip every time. (7) Repeat Step 4.6 with loads of 1.35N and 1.8N. (8) Remove the flue and replace with another 35 kHz Extended Length 60 Durometer Flue. Repeat Steps 4.2-4.7 until three 35 kHz Extended Length 60 Durometer Flues have been tested.

Figure 28A:
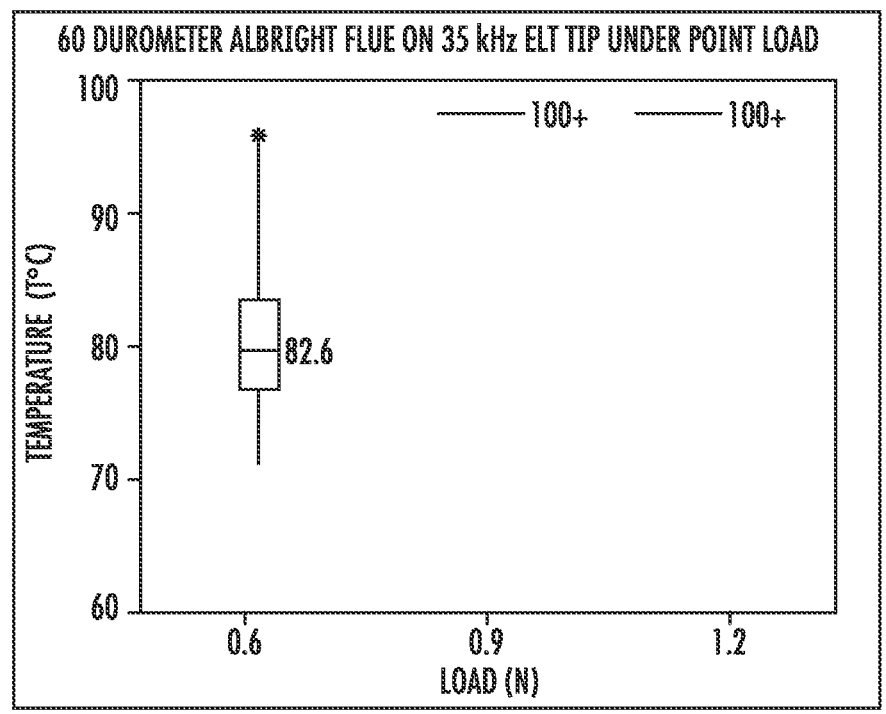
FIG. 28A shows point load thermal data of the baseline flue.
Figure 28B:
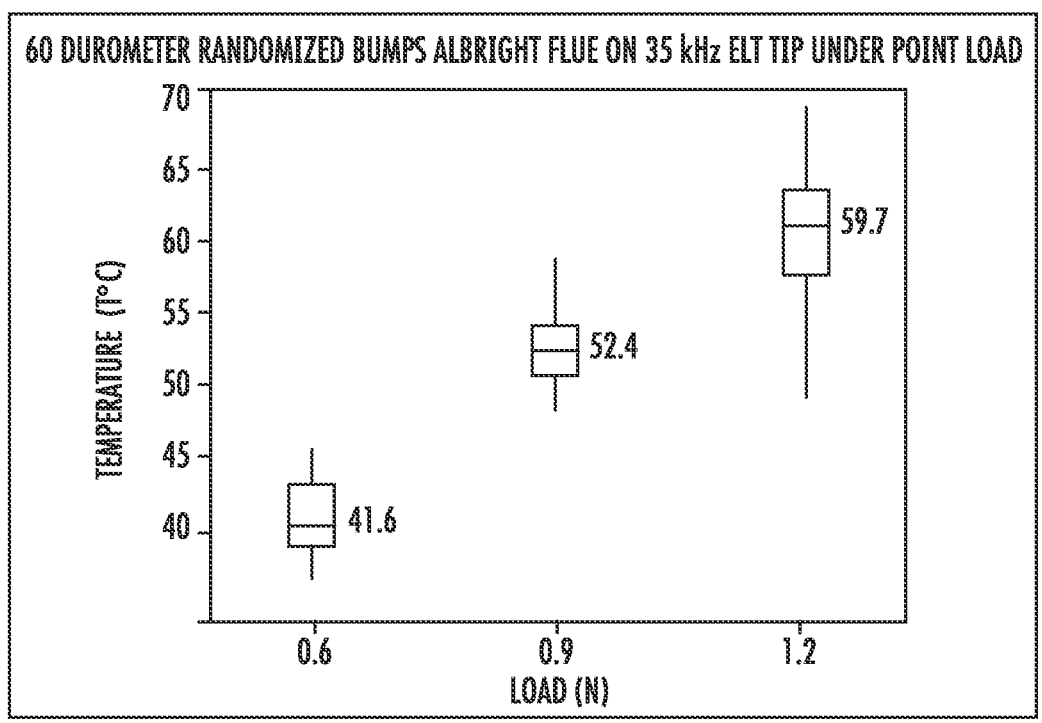
FIG. 28B shows point load thermal data of an embodiment of the flue in accordance with the present invention.
Figure 29A:
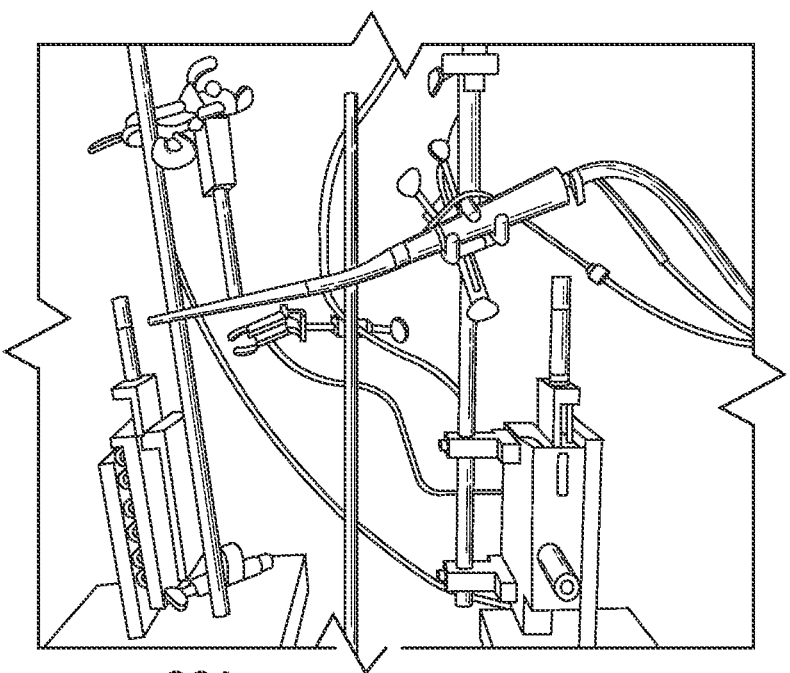
FIGS. 29A, 29B, 29C, and 29D show the equipment used in the additional point load test, wherein a thermocouple surrounded by less thermally conductive material is utilized.
Figure 29B:
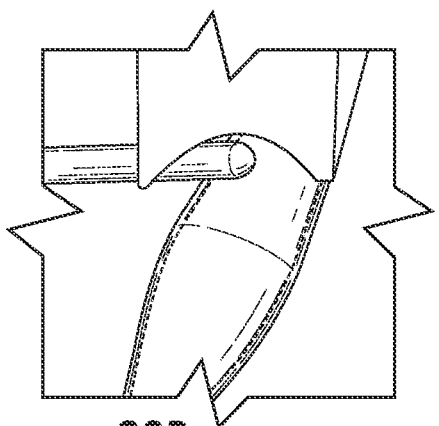
Figure 29C:
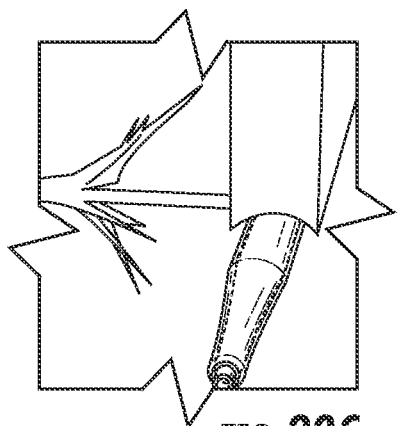
Figure 29D:
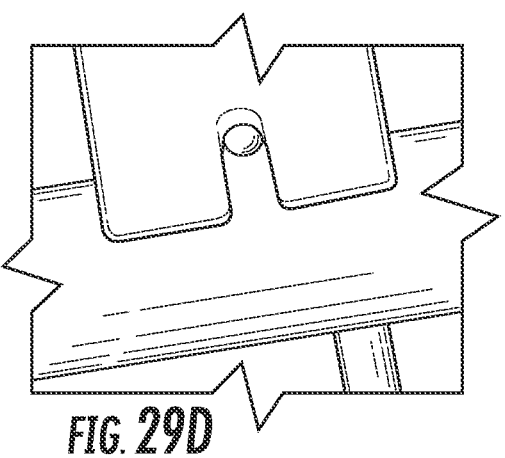

As shown in FIGS. 28A (for a conventional flue) and 28B (for a flue according to the resent invention), under point loading conditions, 60 durometer flues configured in accordance with the present invention exhibited greatly reduced temperatures with the protrusions of greater density and improved pattern. It was noted that it took greater than 30 seconds or more for maximum temperatures to be obtained. The flue would have to be compressed at a region yielding high temperatures at an excessive load for a prolonged period of time. Improvement was noted in reduced temperature with the improved protrusion pattern of greater density.

Example 6. Additional Point Load Testing

Figure 30:
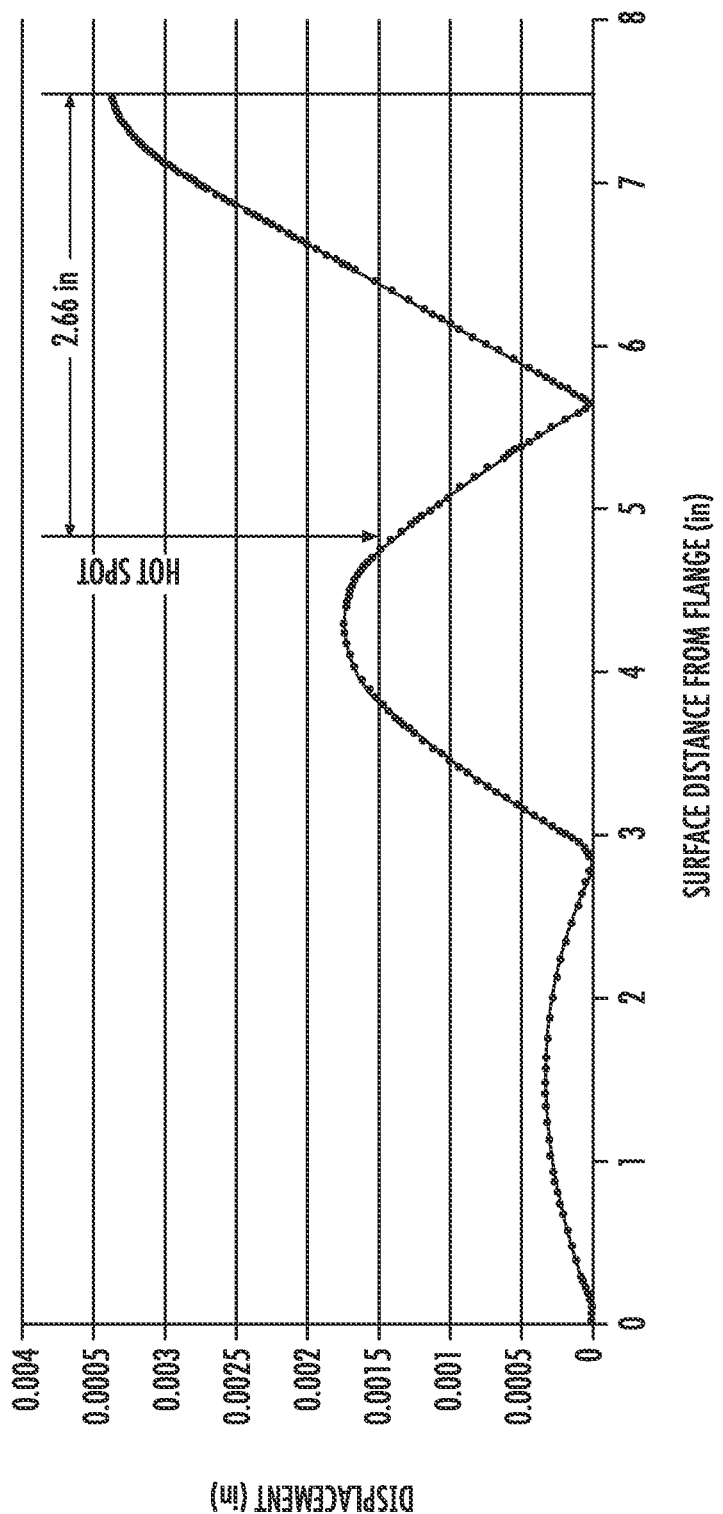
FIG. 30 shows the result of the additional point load test.

A worst case test is performed, as shown in FIGS. 29A-D, with essentially a point load of a thermocouple surrounded by less thermally conductive material. Additionally, a static load is assumed in assessing temperature after a prolonged period, such as if the surgeon were to keep the surgical tip and flue in specific position for a significant amount of time. As shown in FIG. 30, hot spots on the flue outside surface of maximum temperature with point load applied were previously probed. In this case, the maximum temperature was found to be beyond the antinode of the small extender. The hottest spot could be at maximum due to being beyond the greatest motion point and within a high strain gradient region. Further testing to associate this point with the strain gradient maxima may be performed. It is clear that the thermal maximum is beyond the antinode, and this discovery of hot spots at other than the antinode and implementation of the expanded region of greater density of protrusions is the principle of the patent application and improved design of new silicone flues.

Initial comparative test results are provided. For the comparative testing, 100% amplitude, 3 ml/min, and 100% aspiration was used for the Curved Extended MicroTip Plus surgical tip. These data in Table 3 for each load combines measurements of different materials and finishes. Improvements of greater than 20% are noted for the worst case point loading. It should be noted, different durometers surfaces finishes, and silicone materials were assessed in the testing. Earlier testing included different fabrication processes. Additionally, study was done of PTFE coated silicone. The protrusions were the dominant effect on temperature rise, so the existing 60 durometer commercial rating is employed along with Dow Corning Silicone without coatings.

TABLE 3

Average Maximum Temperatures Under Point Load

| Force [N] | Avg T_max, commercial [° C.] | Avg T_max, new design [° C.] | Difference [° C.] |
|---|---|---|---|
| 0.3 | 34.4 | 26.5 | 7.9 |
| 0.6 | 40.6 | 30.0 | 10.6 |
| 1.0 | 65.0 | 41.5 | 23.5 |
| 2.0 | 100.8 | 70.3 | 30.5 |

Figure 31:
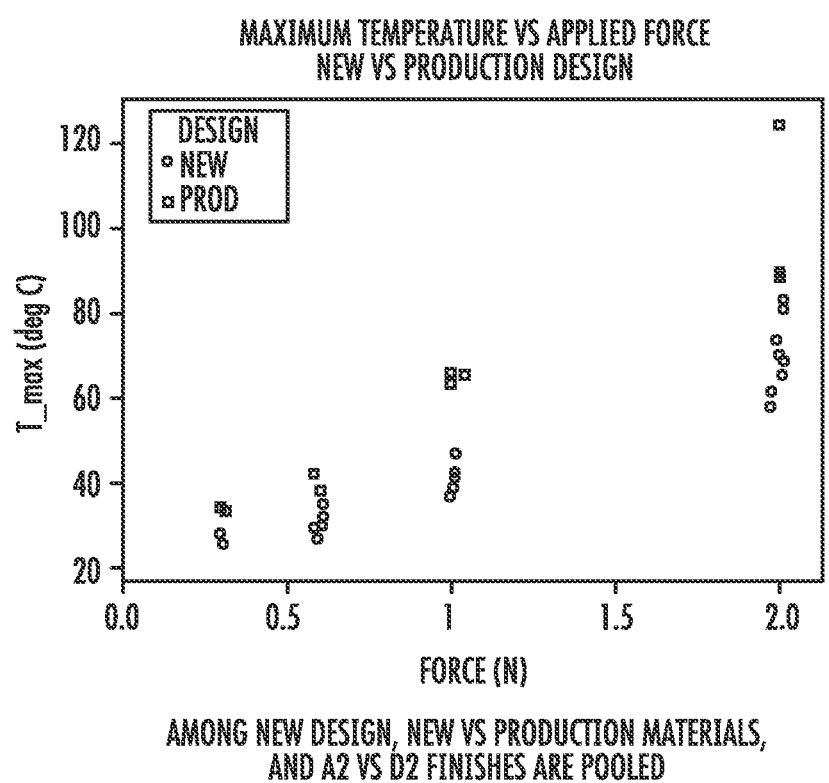
FIG. 31 shows the result of worse case point load testing.

The influence of loading on thermal rise was assessed beyond expected forces in endonasal applications where there have been some complaints regarding potentials burns of tissue. These data are shown in FIG. 31, for very high loading. The benefit of the flue design is prevalent at high loads. Reduced thermal rise were observed at all lateral loads. In this testing, the result indicated greater than 20% improvement.

Studies indicated that point loading provided a worst case comparison of flue designs for thermal rise under increased forces, while distributed load may be more like the clinical case, and less demanding due to somewhat compliant tissue that has been indicated at potential burn sites.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

The invention claimed is:

1. A flue for an ultrasonic surgical apparatus, comprising:
an internal surface including first region and a plurality of protrusions, wherein the plurality of protrusions form a bridge that limits contact with the first region of the internal surface; and
a first flue extender portion and a second flue extender portion extending from the first flue extender portion, and wherein the second flue extender portion has a higher density of the plurality of protrusions than the first flue extender portion.

2. The flue of claim 1, wherein the plurality of protrusions of the first flue extender portion or the plurality of protrusions of the second flue extender portion form the bridge at least longitudinally or axially.

3. The flue of claim 1, wherein an average height of the plurality of protrusions of the first flue extender portion comprises a range of about 0.02 inches to about 0.06 inches, and the average height of the plurality of protrusions of the second flue extender portion comprises a range of about 0.01 inches to about 0.03 inches.

4. The flue of claim 1, further comprising a third flue extender portion extending distally from the second flue extender portion, the third flue extender portion comprising a plurality of ribs on the internal surface of the flue.

5. The flue of claim 1, wherein a size and a shape of the plurality of protrusions of the first flue extender portion are different, or the size and the shape of the plurality of protrusions of the second flue extender portion are different.

6. The flue of claim 1, wherein the plurality of protrusions are distributed in staggered rows and columns.

7. An ultrasonic surgical apparatus comprising:
an ultrasonic horn having an external surface; and
a flue having an internal surface, wherein the flue is configured to be disposed about the external surface of the ultrasonic horn;
wherein the internal surface of each one of a first flue extender portion and a second flue extender portion includes a region defining a first inner diameter and a plurality of protrusions projecting inwardly from the region defining a second inner diameter, and wherein the plurality of protrusions form a bridge that limits contact between the region of the internal surface of the flue and the external surface of the ultrasonic horn.

8. The ultrasonic surgical apparatus of claim 7, wherein the plurality of protrusions of the first flue extender portion have a spherical radius in the range of 0.01 inches to 0.10 inches, and the plurality of protrusions of the second flue extender portion have a spherical radius in the range of 0.01 inches to 0.08 inches.

9. The ultrasonic surgical apparatus of claim 7, wherein the plurality of protrusions of the first flue extender portion are smaller than the plurality of protrusions of the second flue extender portion.

10. The ultrasonic surgical apparatus of claim 7, wherein the second inner diameter is smaller than the first inner diameter.

11. The ultrasonic surgical apparatus of claim 7, wherein the second flue extender portion comprises a higher density of the plurality of protrusions than the first flue extender portion.

12. The ultrasonic surgical apparatus of claim 7, wherein the plurality of protrusions of the first flue extender portion or the plurality of protrusions of the second flue extender portion form the bridge at least longitudinally or axially.

13. A flue for an ultrasonic surgical apparatus, comprising:
an internal surface extending between a first end and a second end; and
a first flue extender portion and a second flue extender portion extending between the first end and the second end;
wherein the internal surface of each one of the first flue extender portion and the second flue extender portion includes an arcuate region defining a first inner diameter and a plurality of protrusions projecting inwardly from the arcuate region defining a second inner diameter, wherein the second inner diameter is smaller than the first inner diameter; and
wherein the second flue extender portion has a higher density of the plurality of protrusions than the first flue extender portion.

14. The flue of claim 13, wherein an average height of the plurality of protrusions of the first flue extender portion comprises a range of about 0.02 inches to about 0.06 inches, and the average height of the plurality of protrusions of the second flue extender portion comprises a range of about 0.01 inches to about 0.03 inches.

15. The flue of claim 13, wherein the second inner diameter is smaller than the first inner diameter.

16. The flue of claim 13, wherein the plurality of protrusions form a bridge that limits contact with the region of the internal surface.

17. The flue of claim 13, wherein the plurality of protrusions of the first flue extender portion or the plurality of protrusions of the second flue extender portion form the bridge at least longitudinally or axially.

18. The flue of claim 13, wherein the second flue extender portion adjacent the second end extends from the first flue extender portion adjacent the first end.

19. The flue of claim 13, wherein the plurality of protrusions are distributed in staggered rows and columns.

20. The flue of claim 13, wherein a size and a shape of the plurality of protrusions of the first flue extender portion are different, or the size and the shape of the plurality of protrusions of the second flue extender portion are different.

* * * * *